United States Patent
Sakurai et al.

(10) Patent No.: US 7,938,779 B2
(45) Date of Patent: May 10, 2011

(54) TREATING APPARATUS AND TREATING DEVICE FOR TREATING LIVING-BODY TISSUE

(75) Inventors: Tomohisa Sakurai, Sagamihara (JP); Koji Iida, Sagamihara (JP); Hiroyuki Takahashi, Akishima (JP); Eiji Murakami, Hachioji (JP); Akihisa Ogawa, Hino (JP); Kenji Noda, Machida (JP); Seiichi Hosoda, Hino (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 1911 days.

(21) Appl. No.: 11/011,899

(22) Filed: Dec. 14, 2004

(65) Prior Publication Data

US 2005/0101945 A1     May 12, 2005

Related U.S. Application Data

(63) Continuation of application No. 10/272,127, filed on Oct. 16, 2002, now abandoned.

(30) Foreign Application Priority Data

Oct. 16, 2001 (JP) ................... 2001-318435
Oct. 24, 2001 (JP) ................... 2001-326684

(51) Int. Cl.
  *A61B 8/00* (2006.01)
(52) U.S. Cl. ............... 600/439; 606/28; 606/31; 606/34
(58) Field of Classification Search ............ 601/2, 3; 606/1, 37–41, 45–51, 10–12, 32–35; 604/22; 600/439
See application file for complete search history.

(56) References Cited

U.S. PATENT DOCUMENTS

| | | | |
|---|---|---|---|
| 4,074,719 A | | 2/1978 | Semm |
| 4,685,459 A | | 8/1987 | Koch et al. |
| 5,013,312 A | | 5/1991 | Parins et al. |
| 5,122,137 A | * | 6/1992 | Lennox ............ 606/40 |
| 5,462,522 A | * | 10/1995 | Sakurai et al. ........ 604/22 |
| 5,496,312 A | * | 3/1996 | Klicek ............ 606/34 |
| 5,562,503 A | * | 10/1996 | Ellman et al. .......... 439/638 |
| 5,593,406 A | * | 1/1997 | Eggers et al. .......... 606/29 |
| 5,611,798 A | | 3/1997 | Eggers |

(Continued)

FOREIGN PATENT DOCUMENTS

JP     4-212338     8/1992

(Continued)

*Primary Examiner* — Long V Le
*Assistant Examiner* — Sanjay Cattungal
(74) *Attorney, Agent, or Firm* — Scully, Scott, Murphy & Presser, P.C.

(57) ABSTRACT

In a treating apparatus, a forceps body as a treating device is connected to a generator as a control device. The forceps body mainly includes a pair of handle portions, which are used for manipulation by being held by an operator, a pair of jaws provided between the handle portion and the pair of jaws, which are used to coagulate/resect by grasping living-body tissue to be treated and a pair of scissors component members. A heating member, which is a heat generating source as a heat generating portion for applying heat energy to living-body tissue, is embedded at least one of the jaws. A pair of electrode portions, which is a treating energy generator, is provided to the pair of jaws. By supplying bipolar electric surgical knife current between the pair of electrode portions, high frequency current as treating energy is applied to the grasped living-body tissue.

13 Claims, 17 Drawing Sheets

U.S. PATENT DOCUMENTS

| | | |
|---|---|---|
| 5,624,452 A | 4/1997 | Yates |
| 5,707,369 A * | 1/1998 | Vaitekunas et al. ............ 606/31 |
| 5,792,137 A | 8/1998 | Carr et al. |
| 5,836,897 A * | 11/1998 | Sakurai et al. .................... 601/2 |
| 6,174,309 B1 * | 1/2001 | Wrublewski et al. ........... 606/45 |
| 6,228,080 B1 | 5/2001 | Gines |
| 6,235,027 B1 * | 5/2001 | Herzon ............................ 606/51 |
| 6,273,886 B1 * | 8/2001 | Edwards et al. ................. 606/34 |
| 6,454,781 B1 * | 9/2002 | Witt et al. ...................... 606/169 |
| 6,626,901 B1 * | 9/2003 | Treat et al. ...................... 606/29 |
| 6,666,860 B1 * | 12/2003 | Takahashi ........................ 606/34 |
| 6,908,463 B2 * | 6/2005 | Treat et al. ...................... 606/29 |
| 7,108,695 B2 * | 9/2006 | Witt et al. ....................... 606/41 |
| 7,211,079 B2 * | 5/2007 | Treat ............................... 606/29 |
| 7,255,697 B2 * | 8/2007 | Dycus et al. .................... 606/49 |
| 7,406,970 B2 * | 8/2008 | Zikorus et al. ................ 128/898 |
| 2002/0082593 A1 * | 6/2002 | Hareyama et al. .............. 606/38 |
| 2003/0073987 A1 * | 4/2003 | Sakurai et al. .................. 606/28 |
| 2007/0244477 A1 * | 10/2007 | Santilli et al. ................... 606/29 |

FOREIGN PATENT DOCUMENTS

| | | |
|---|---|---|
| JP | 5-220157 | 8/1993 |
| JP | 6-311988 | 11/1994 |
| JP | 2000-070280 | 3/2000 |
| JP | 2000-254136 | 9/2000 |
| JP | 2000-296135 | 10/2000 |
| JP | 2001-190561 | 7/2001 |
| JP | 2001-190562 | 7/2001 |
| JP | 2002-085420 | 3/2002 |
| JP | 2001-48583 | 9/2002 |
| WO | WO 99/65406 | 12/1999 |

* cited by examiner

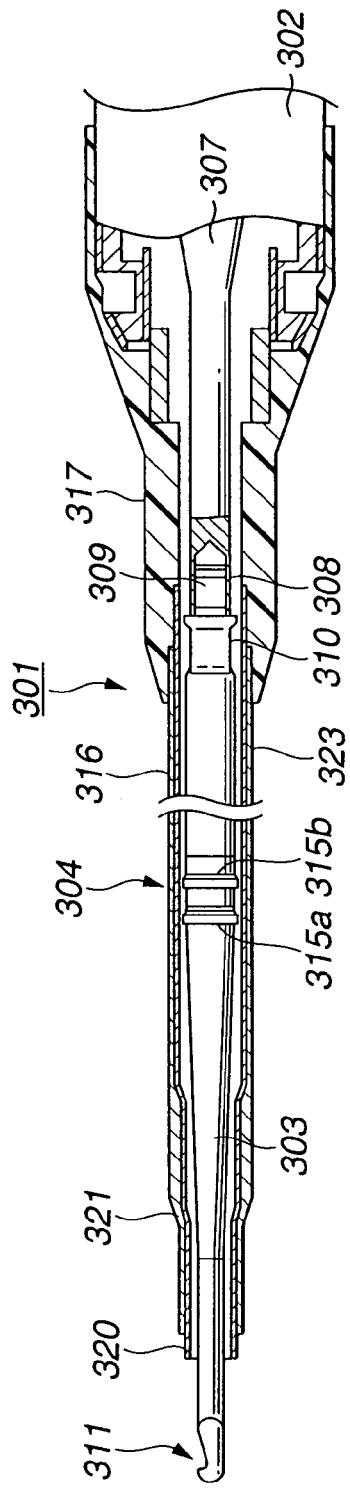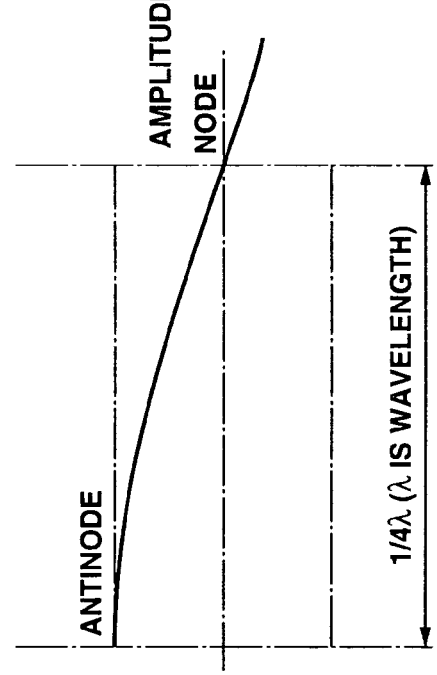

TREATING APPARATUS AND TREATING DEVICE FOR TREATING LIVING-BODY TISSUE

This application is a continuation application of U.S. Ser. No. 10/272,127, filed on Oct. 16, 2002 now abandoned which claims benefit of Japanese Application No. 2001-318435 filed in Japan on Oct. 16, 2001, and No. 2001-326684 filed in Japan on Oct. 24, 2001, the contents of each of which are incorporated herein by this reference.

BACKGROUND OF THE INVENTION

1. Field of the Invention

The present invention relates to a treating apparatus and a treating device, which are used to coagulate or resect by heating living-body tissue.

2. Description of the Related Art

Conventionally, a medical treating apparatus is used to coagulate or resect by heating living-body tissue. For example, a coagulation treating device, a bipolar treating device, an ultrasound treating device and so on are known as treating devices used for the medical treating apparatus.

The coagulation treating device is used to coagulate or resect by heating living-body tissue, across which heaters as heat generating portions are provided at a distal end portion of a forceps. The bipolar treating device is used to coagulate living-body tissue by holding the living-body tissue between a pair of forceps and then flowing high frequency current therebetween. The ultrasound treating device is used to coagulate or resect by supplying ultrasound vibration to the distal end of the forceps to generate frictional heat within the held living-body tissue.

The coagulation treating device may be a thermal coagulation treating device having a heater as a heat generating portion at a resecting portion at the distal end of forceps, which is disclosed in the U.S. Pat. No. 5,792,137. Alternatively, the coagulation treating device may be a coagulation treating device, which is used to coagulate living-body tissue by using a heater provided as a heat generating portion at a distal end jaw part, which is disclosed in Japanese Unexamined Patent Application Publication No. 2001-190562.

In the coagulation treating device for coagulating living-body tissue by using a heater, it is easy to control a heating temperature on living-body tissue unlike the bipolar treating device. In addition, the coagulation treating device hardly sticks to living-body tissue because evaporation and cauterization of living-body tissue due to a rapid temperature change is not caused. Furthermore, the coagulation treating device has a feature that the thin and curved distal-end treating portion can be produced easily unlike the ultrasound treating device.

However, the conventional coagulation treating device generates thermal energy by a small heating member provided at the distal end portion of the forceps, which supplies heat to living-body tissue. Therefore, the conventional coagulation treating device can function satisfactorily with a thermal amount generated by the heating member if the living-body tissue to be coagulated is separated enough from the surrounding tissue or if the living-body tissue to be coagulated is dry in the progress of an operation. However, the living-body tissue cannot be coagulated efficiently because heat is diffused at the distal end of the forceps holding the living-body tissue if the living-body tissue to be coagulated cannot be separated from the surrounding tissue enough, or if the surrounding tissue is also needed to coagulate together, or if blood and/or body fluid stagnate around the living-body tissue to be coagulated. Thus, it takes time to complete the coagulation.

The ultrasound treating device has been proposed which is used to treat an affected part by touching the living-body tissue with the distal end treating portion, which gives ultrasound violation, as disclosed in the Japanese Unexamined Patent Application Publication No. Hei 4-212338 and Unexamined Patent Application Publication No. 2000-254136, for example.

The ultrasound treating device disclosed in the Japanese Unexamined Patent Application Publication No. Hei 4-212338 has a probe for transmitting ultrasound vibration, whose distal end portion is processed into a flat-plane form. In addition, a concave part (hook part) is formed therein. On the other hand, the ultrasound treating device disclosed in Japanese Unexamined Patent Application Publication No. 2000-254136 can be used not only for ultrasound treatment but also for treatment by high frequency current passage.

The ultrasound treating device disclosed in U.S. Pat. No. 5,013,312 has an ultrasound converter in the proximal end of a bipolar electrode. The bipolar electrode is vibrated with ultrasound such that living-body tissue can be resected. Upon the bipolar energization, the living-body tissue can be coagulated. The ultrasound treating device disclosed in U.S. Pat. No. 5,013,312 has an advantage that the ultrasound vibration can prevent living-body tissue from burning onto the bipolar electrode.

An ultrasound treating device disclosed in WO 99/65406 proposes a treating device whereby living-body tissue can be coagulated by using a heating unit (thick film heater pattern).

Furthermore, some ultrasound treating apparatus can perform treatment such as resection and coagulation of living-body tissue by using ultrasound energy. The ultrasound treating apparatus is proposed for treatment through ultrasound vibration by holding living-body tissue, as disclosed in Japanese Unexamined Patent Application Publication No. 2000-296135 and No. 2002-085420. The ultrasound treating apparatus disclosed in the Japanese Unexamined Patent Application Publication No. 2002-085420 is proposed as having a heat generating portion at the movable grasp portion.

On the other hand, a conventional surgical resector is proposed as resecting the meniscus and/or the cartilage by using a resecting blade, which rotates within an external tube for treatment on joint cavity as disclosed in the Japanese Unexamined Patent Application Publication No. Hei 5-220157 and No. Hei 6-311988.

However, each of the surgical resectors disclosed in the Japanese Unexamined Patent Application Publication No. Hei 5-220157 and No. Hei 6-311988 causes bleeding from capillary when living-body tissue is resected. Therefore, the surgical resector disclosed in the Japanese Unexamined Patent Application Publication No. Hei 6-311988 prevents it by applying high frequency current to the resecting blade.

A surgical resector having a heat generating portion at the distal end portion of a long and narrow inserting portion for the uses for allergy therapy is proposed as disclosed in the Japanese Patent Application No. 2001-48583, which is filed by the present applicant before.

However, each of the ultrasound treating devices disclosed in the Japanese Unexamined Patent Application Publication No. Hei 4-212338, No. 2000-254136 and U.S. Pat. No. 5,013,312 is used to treat living-body tissue and has a problem that homeostasis coagulation of living-body tissue takes time.

The ultrasound treating device disclosed in the WO 99/65406 performs fluropolymers coating in order to prevent living-body tissue from burning on due to the lack of ultrasound vibrator. Thus, the ultrasound treating device disclosed in the WO 99/65406 has a problem of low durability.

The ultrasound treating apparatus disclosed in the Japanese Unexamined Patent Application Publication No. 2000-296135 only can perform ultrasound treatment. Therefore, coagulation takes time or the operability is low when only coagulation is performed because the resection action also works together with the coagulation.

Thus, the ultrasound treating apparatus disclosed in the Japanese Unexamined Patent Publication No. 2000-296135 includes a heat generating portion at the removable grasp portion, which improves the coagulation power. However, the ultrasound treating apparatus disclosed in the Japanese Unexamined Patent Application Publication No. 2000-296135 requires another energizing unit for the heat generating portion at the removable grasp portion in addition to the energizing unit for the ultrasound vibrator, resulting in a more complicated structure.

In the surgical resector disclosed in the Japanese Unexamined Patent Application No. Hei 6-311988, noise is easy to mix into a motor drive circuit, for example, due to the energization of high frequency current. Therefore, the surgical resector disclosed in the Japanese Unexamined Patent Publication No. 6-311988 needs a measure against the noise, which causes the structure more complicated. Furthermore, the surgical resector disclosed in the Japanese. Unexamined Patent Application Publication No. 2001-48583 performs allergy treatment within a nose. Thus, living-body tissue such as cartilage cannot be resected.

In addition, a coagulation treating device, which can reset and staple (integration or joint) while stopping bleeding, is proposed, as disclosed in U.S. Pat. No. 5,624,452.

As disclosed in U.S. Pat. No. 5,611,798, a proposed coagulation treating device has a heat generating portion at the distal end and has 200° C./W or more of thermal resistance value at a part associating with living-body tissue and 100° C./W or less of thermal resistance value at a supporting portion of the engaged part. Thus, the heat influence when resecting living-body tissue can be reduced.

As disclosed in U.S. Pat. No. 4,074,719, for example, a proposed coagulation treating device has a control device for controlling a current supply unit, which is used to increase a temperature of a thermal element provided at the end with a predetermined temperature gradient until the temperature reaches to the temperature level which causes coagulation. After reaching to the temperature level, the temperature is maintained steadily. In addition, a freely audible instruction unit is provided thereto, which increases the strength of sound in accordance with the heat gradient until the temperature of the thermal element reaches to the temperature level. After the temperature of the thermal element reaches to the temperature level, a certain strength of sound is generated.

Furthermore, as disclosed in U.S. Pat. No. 6,228,080, for example, a proposed bipolar treating device applies an output again when the tissue impedance of living-body tissue does not indicate dry and adjusts the excess output in accordance with a degree of dryness of the living-body tissue.

As disclosed in U.S. Pat. No. 4,685,459, for example, a proposed bipolar treating device has a temperature sensor in the treating portion so as to display a temperature of a subject part and to control the temperature.

As disclosed in U.S. Pat. No. 5,707,369, for example, a proposed bipolar treating device has a temperature measuring unit and a comparing unit for comparing a changed amount in times and a threshold value so as to, for example, change an output control method for automatically stopping coagulation, for example.

As disclosed in U.S. Pat. No. 5,496,312, a proposed bipolar treating device has a detecting unit for detecting impedance or a temperature for every multiple active electrodes. Thus, the output control method can be changed so as to control in accordance with the detected value individually and independently.

As disclosed in U.S. Pat. No. 5,122,137, for example, a proposed bipolar treating device includes an RF conductor and an RF medical device, first and second pole connecting units, a temperature sensor and a control circuit. When RF output is not performed, a temperature is detected and the temperature in coagulation is controlled by controlling RF output.

SUMMARY OF THE INVENTION

Accordingly, it is an object of the present invention to provide a treating apparatus and a treating device, which can coagulate and resect living-body tissue efficiently in any operation cases without making a distal end treating portion large.

It is another object of the present invention to provide a treating apparatus and a treating device, which can perform coagulation treatment in addition to ultrasound treatment or high frequency treatment efficiently without conducting current to living-body tissue.

It is another object of the present invention to provide a treating apparatus and a treating device, which can perform coagulation, resection and the like on living-body tissue selectively by using energy corresponding to ultrasound treatment or high frequency treatment and heat generating treatment.

It is another object of the present invention to provide a treating apparatus and a treating device, which can perform ultrasound treatment or high frequency treatment after coagulation without conducting current to living-body tissue during coagulation. Thus, burning onto living-body tissue can be prevented.

According to an aspect of the present invention, there is provided a treating apparatus for treating living-body tissue, including a treating device having a heat generating portion for generating heat to be applied to the living-body tissue and a treating energy generator for generating treating energy different from the heat, the treating device contacting with the living-body tissue and applying the heat generated by the heat generating portion and the treating energy generated by the treating energy generator to the living-body tissue, and a control device for controlling the heat generating portion or the treating energy generator of the treating device.

According to another aspect of the present invention, there is provided a treating device for treating living-body tissue, including a heat generating portion for generating heat to be applied to the living-body tissue, a high frequency electrode for generating high frequency current to be applied to the living-body tissue, a treating portion for contacting the living-body tissue and applying, to the living-body tissue, the heat generated by the heat generating portion and the high frequency current generated by the high frequency electrode, and a pair of jaws having the treating portion and including the heat generating portion or the high frequency electrode in at least one of the jaws and being supported openably to grasp the living-body tissue.

According to another aspect of the present invention, there is provided a treating device for treating living-body tissue, including a heat generating portion for generating heat to be applied to the living-body tissue, an ultrasound vibrator for generating ultrasound vibration to be applied to the living-body tissue, a treating portion for contacting the living-body tissue and applying, to the living-body tissue, the heat generated by the heat generating portion and the ultrasound vibration generated by the ultrasound vibrator, and a probe having the treating portion and conducting the heat generated by the heat generating portion and the ultrasound vibration generated by the ultrasound vibrator.

These and the other features and advantages will be fully apparent from the following description.

BRIEF DESCRIPTION OF THE DRAWINGS

FIG. 9A is a sectional view of an essential part of the ultrasound treating device of FIG. 8;

FIG. 9B is a diagram showing a relationship between amplitude and a wavelength of FIG. 9A;

FIG. 9C is a developed view of a flexible substrate of FIG. 9A;

FIG. 9D is a sectional view of the flexible substrate of FIG. 9C;

DESCRIPTION OF THE PREFERRED EMBODIMENTS

Embodiments of the present invention will be described below with reference to drawings.

First Embodiment

Figure 1:
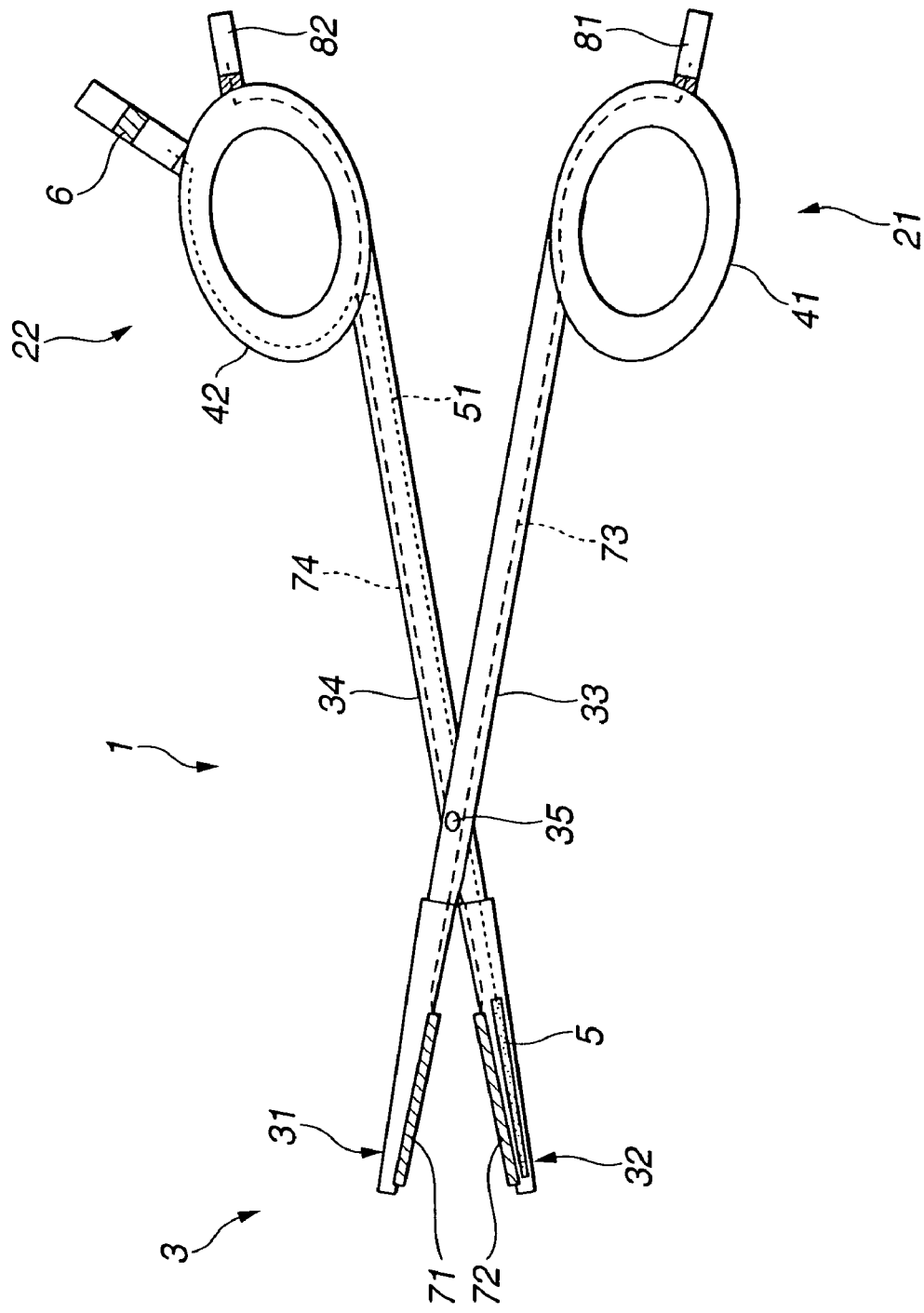
FIG. 1 is a front view of a forceps body according to a first embodiment of the present invention.
Figure 2:
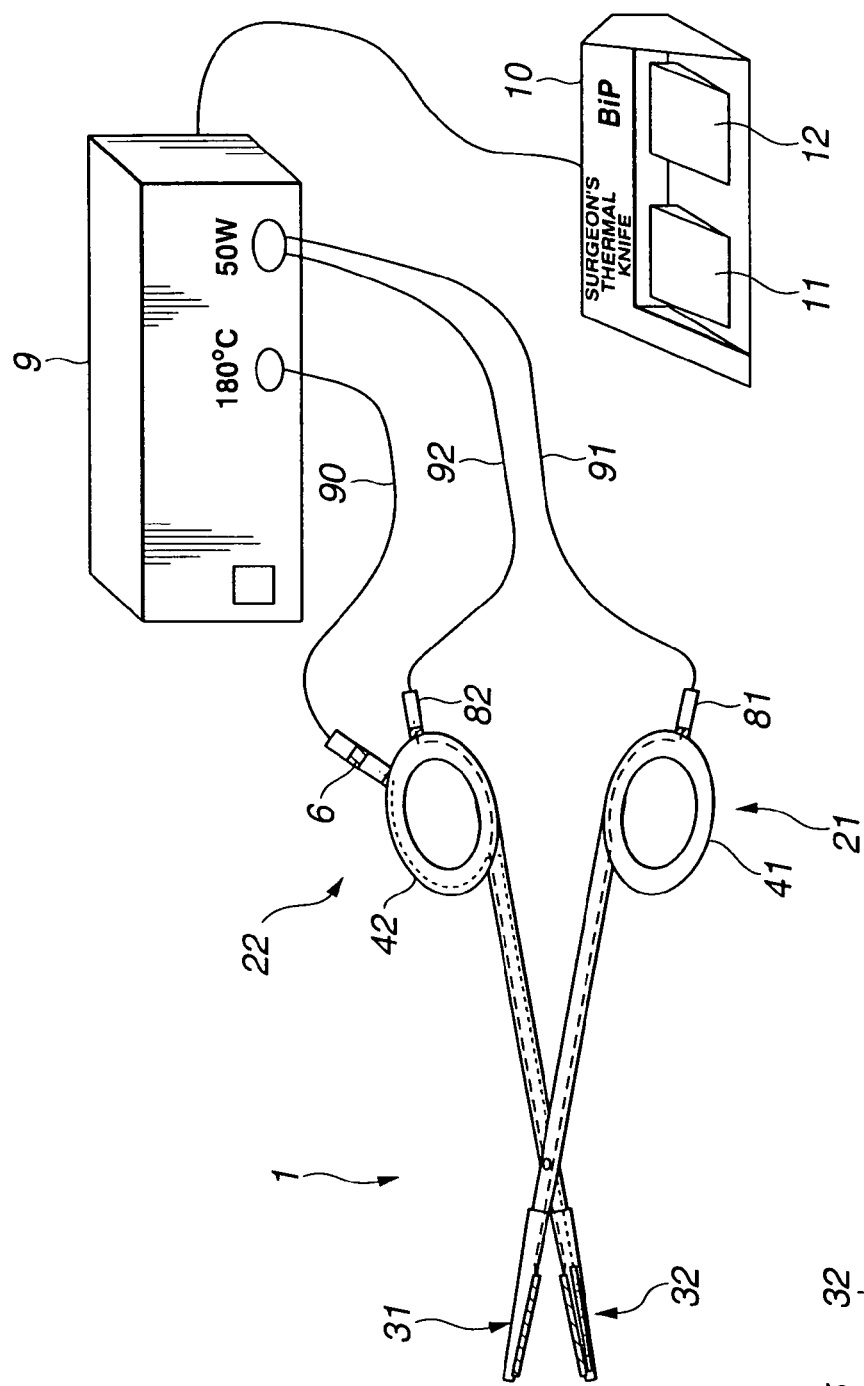
FIG. 2 is an entire configuration diagram showing a treating apparatus in which a generator is connected to the forceps body of FIG. 1.

FIGS. 1 and 2 relate to a first embodiment of the present invention. FIG. 1 is a plan view of a forceps body. FIG. 2 is an entire configuration diagram showing a treating apparatus in which a generator is connected to a forceps body 1 of FIG. 1.

First of all, the forceps body 1, which is a surgical treating device according to the present invention, will be described with reference to FIG. 1.

As shown in FIG. 1, the forceps body 1 mainly includes a pair of handle portions 21 and 22, which are used for manipulation with being held by an operator, a pair of jaws 31 and 32, which are used to coagulate/resect by grasping living-body tissue to be treated and a pair of scissors component members 33 and 34.

The jaws 31 and 32 form a distal end treating portion 3 of the forceps body 1.

The pair of scissors component members 33 and 34 is provided between handle portions 21 and 22 and the jaws 31 and 32. The scissors component members 33 and 34 are overlapped by intersecting the middle parts. The intersecting part of the scissors component members 33 and 34 is provided with a fulcrum pin 35, which joints the scissors component members 33 and 34 freely rotatably.

The handle portions 21 and 22 are provided with rings 41 and 42, which are held by fingers. The jaws 31 and 32 in the forceps body 1 are open or closed in connection with open or close operations by putting a thumb and a middle finger through the rings 41 and 42, respectively.

A heating member, which is a heat generating source for supplying thermal energy to living-body tissue is embedded in the jaw 32. The scissors component member 34 is provided inside with a power supply line 51 for supplying electric signals to the heating member 5. The power supply line 51 extends from the jaw 32 to the handle portion 22. The ring 42 is provided with a thermal surgical knife terminal 6. The thermal surgical knife terminal 6 is connected to the power supply line 51 electrically.

With the above construction, the heating member 5 can form a heat generating portion for generating heat, which can be supplied for coagulating living-body tissue grasped by at least one of the jaws 31 and 32. The pair of jaws 31 and 32 is supported so as to open and close to grasp the living-body tissue.

The jaws 31 and 32 are provided with electrode portions 71 and 72, respectively, as a pair to be used as a treating energy generator. In the forceps body 1, energy can be supplied to living-body tissue grasped by the jaws 31 and 32 by flowing bipolar electric surgical knife current between the electrode portions 71 and 72.

The scissors component members 33 and 34 are provided inside with power supply lines 73 and 74 for supplying electric signals to the electrode portions 71 and 72, respectively. The power supply lines 73 and 74 extend from the jaws 31 and 32 to the handle portions 21 and 22, respectively. The rings 41 and 42 are provided with bipolar terminals 81 and 82, respectively, the bipolar terminals 81 and 82 are connected to the power supply lines 73 and 74 electrically.

With the above construction, the electrode portions 71 and 72 are provided to the jaws 31 and 32, respectively. The electrode portions 71 and 72 can be a pair of high frequency electrodes, which can supply high frequency current for treating the living-body tissue.

Next, FIG. 2 shows an entire construction of a treating apparatus in which a generator 9 is connected as a control device to the above-described forceps body 1. The generator 9 is energy power supply for the jaws 31 and 32.

The thermal surgical knife terminal 6, and the bipolar terminals 81 and 82 of the forceps body 1 are connected to output terminals of the generator 9 through cords 90, 91 and 92, respectively.

A foot switch 10 is connected to the generator 9. The foot switch 10 is provided with a pedal 11 in the thermal surgical knife side, which is an operating portion for the thermal surgical knife, and a pedal 12 in the bipolar side, which is a bipolar operating portion. An operator can turn ON/OFF treatment by using the foot switch 10.

A method of using the forceps body 1 and the generator 9 included in the treating apparatus will be described below.

An operator manipulates the forceps body 1 by holding the handle portions 21 and 22 and peels living-body tissue to be coagulated/resected. Then, the living-body tissue is grasped and held by using the jaws 31 and 32. After that, the operator steps on the pedal 11 in the thermal surgical knife side of the foot switch 10 to supply current from the generator 9 to the heating member 5 for the thermal surgical knife. Then, heat is generated in the heating member 5, and the operator manipulates so as to coagulate living-body tissue grasped by the jaws 31 and 32.

In general, when heat is continuously given to the living-body tissue, the temperature increases gradually to coagulate the living-body tissue properly. The temperature at that time is about 80° C. The temperature of the living-body tissue is increased to about 150° C. by continuing to give heat thereto. Thus, a separating action is caused in the living-body tissue, and the forceps body 1 can resect the living-body tissue.

However, when an amount of grasped living-body tissue is too much, or when blood or body fluid exists around, the forceps body 1 cannot obtain enough heat to coagulate living-body tissue from thermal energy generated from the heating member 5 for the thermal surgical knife.

In this case, the operator may step on the pedal 12 in the bipolar side continuously. By stepping on the pedal 12 in the bipolar side, bipolar electric surgical knife current can be flown for a short period of time between the electrode portions 71 and 72 provided at the sides of the jaws 31 and 32. Then, the electrode portions 71 and 72 increases the temperature of living-body tissue grasped by the jaws 31 and 32 quickly up to about 60° C. After that, the forceps body 1 and the generator 9 can coagulate the living-body tissue by using heat generated by the heating member 5 for the thermal surgical knife.

According to the first embodiment, the forceps body 1 is provided at the jaw 32 with the heating member 5 for the thermal surgical knife. In addition, electrode portions 71 and 72, which can supply high frequency current to treat living-body tissue, are provided with the jaws 31 and 32, respectively. Thus, the size of the distal end treating portion 3 including the jaws 31 and 32 is not increased. The features of the thermal surgical knife can be used effectively, and, at the same time, the temperature of the distal end treating portion 3 can be increased quickly up to close to the target temperature even under a condition where the temperature of the distal end treating part 3 is hard to increase. Therefore, the forceps body 1 according to the first embodiment has the distal end treating portion 3 including the pair of jaws 31 and 32, which is not so large. Thus, coagulation and resection of living-body tissue can be performed by using the distal end treating portion 3 in any operation cases.

Notably, in the first embodiment shown in FIGS. 1 and 2, the heating member 5 for thermal surgical knife is only provided to the jaw 32. However, the heating member 5 for the thermal surgical knife may be provided to each of the jaws 31 and 32.

Figure 3:
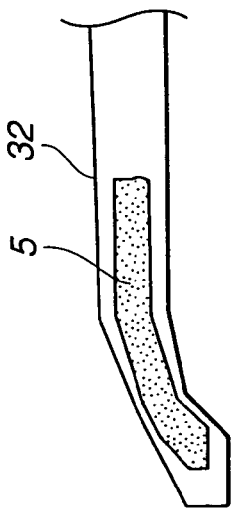
FIG. 3 is an enlarged diagram showing another example of a jaw of FIG. 1.

FIG. 3 is an enlarged diagram showing another example of the jaw 32 shown in FIG. 1.

In FIG. 3, the jaw 32 and the heating member 5 are curved. The jaw 31, not shown, is also curved.

In general, the curved jaws 31 and 32 are easy to use for treatment.

Second Embodiment

Figure 4:
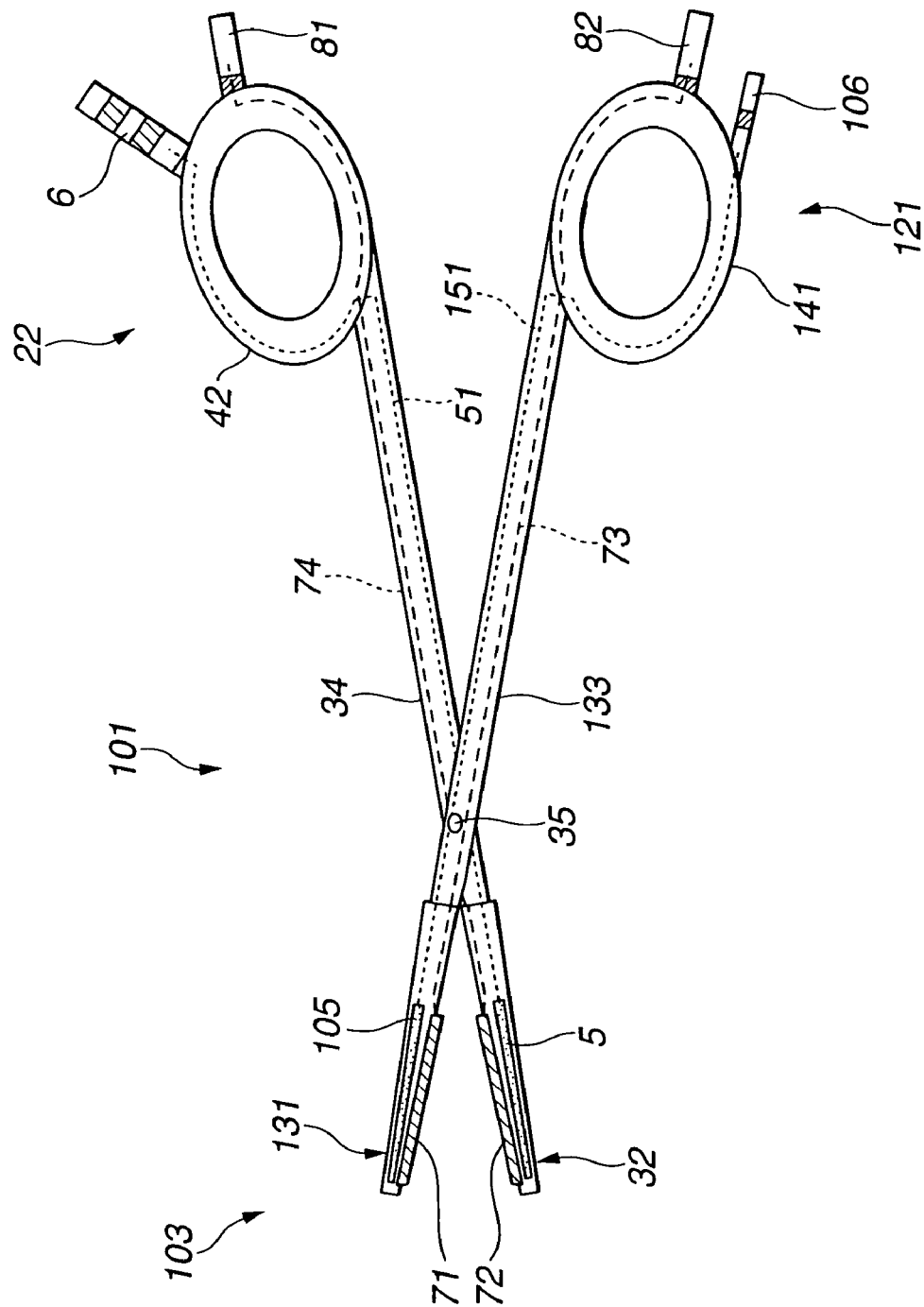
FIG. 4 is a front view of a forceps body according to a second embodiment of the present invention.
Figure 5:
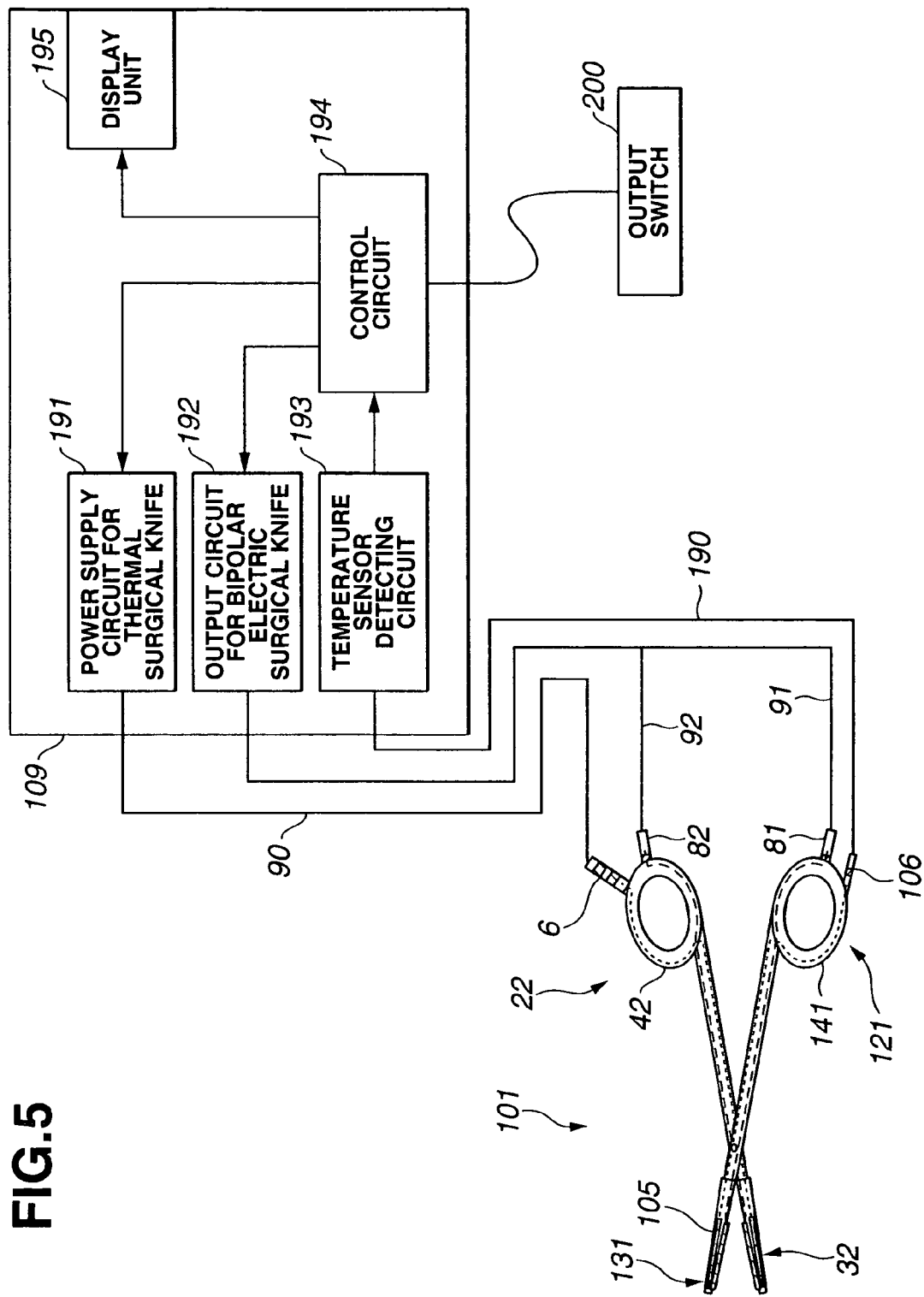
FIG. 5 is an entire configuration diagram showing a treating apparatus in which a generator is connected to a forceps body of FIG. 4.

FIGS. 4 and 5 relate to a second embodiment of the present invention. FIG. 4 is a plan view of a forceps body. FIG. 5 is an entire configuration diagram showing a treating apparatus in which a generator is connected to the forceps body of FIG. 4.

FIG. 4 shows a forceps body 101, which is obtained by improving the treating device described in FIG. 1. Identical reference numerals are given to the identical components of the forceps body 1 in FIG. 1 in the following description.

As shown in FIG. 4, the forceps body 101 according to the second embodiment, a temperature sensor 105 is additionally provided to a jaw 131 of a distal end treating portion 103. In the forceps body 101, a power supply line 151 for supplying electric signals to the temperature sensor 105 extends from the jaw 131 to a handle portion 121 through the inside of a scissors component member 133.

A ring 141 is provided with a sensor terminal 106. The sensor terminal 106 is electrically connected to the power supply line 151.

The construction, which is not described above, is the same as the construction of the forceps body 1 shown in FIG. 1.

As shown in FIG. 5, a generator 109 corresponds to the forceps body 101.

A surgical knife thermal terminal 6, bipolar terminals 81 and 82, the sensor terminal 106 of the forceps body 101 are connected to respective input/output terminals of the generator 9 through cords 90, 91, 92 and 190.

The generator 109 includes a power supply circuit 191 for the thermal surgical knife, an output circuit 192 for the bipolar electric surgical knife, a detecting circuit 193, a control circuit 194 and a display portion 195 at least.

Under the control of the control circuit 194, the power supply circuit 191 for the thermal surgical knife supplies power to the thermal surgical knife terminal 6 through the cord 90.

The output circuit 192 or the bipolar electric surgical knife supplies bipolar high frequency power to bipolar terminals 81 and 82 through the cords 91 and 92.

The detecting circuit 193 detects a temperature from a signal received from the temperature sensor 105 through the cord 190 and supplies the detection result to the control circuit 194.

The display portion 195 performs image-displaying of an apparatus operating state of the generator 109 and the forceps body 101 based on the control by the control circuit 194.

An output switch 200 used to turning ON/OFF the output is connected to the control circuit 194.

The temperature sensor 105 provided in the jaw 131 can measure a temperature of grasped living-body tissue in real time.

The temperature sensor 105 outputs the detected signal to the sensor terminal 106, which is provided in the ring 141, through a line 151 within the scissors component member 133. The detected signal from the sensor terminal 106 is transmitted to the detecting circuit 193 within the generator 109. Thus, the generator 109 can realize the temperature of the jaw 131. The value may be displayed in the display portion 195. According to the second embodiment, a detection signal from the detecting circuit 193 can be used as a feedback signal in the control circuit 194 for the overall control, as described below.

Figure 6:
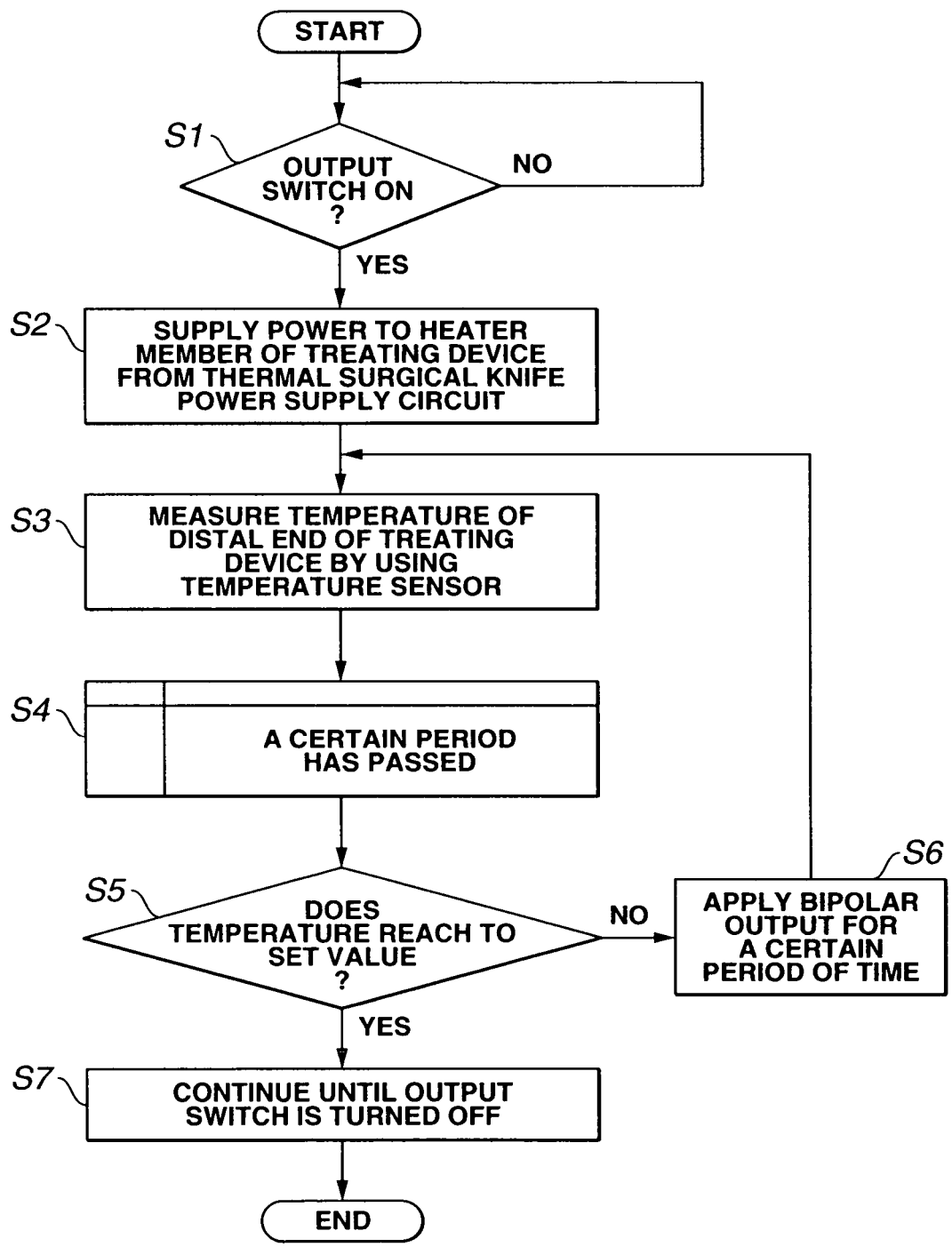
FIG. 6 is a flowchart showing control by a control circuit of FIG. 5.

FIG. 6 is a flowchart showing the control by the control circuit 194 of the generator 109.

A method of using the forceps body 101 and the generator 109 will be described with reference to the flowchart in FIG. 6.

First of all, an operator peels living-body tissue to be coagulated and resected and grasps the peeled living-body tissue by using the jaws 131 and 32. Then, the operator manipulates the output switch 200. As a result, the control circuit 194 determines YES at step 1. Then, the processing moves to step S2.

At step S2, the power supply circuit 191 for the thermal surgical knife supplies power and gives thermal energy to the heating member 5 for the thermal surgical knife of the forceps body 101 under the control of the control circuit 194. Thus, the living-body tissue is heated. During this process, the control circuit 194 controls, at step S3, the detecting circuit 193 to measure a temperature of the treating device distal end 3 by using the temperature sensor 105.

After that, the control circuit 194 waits for a certain period of time at step S4. If the measured temperatures of the jaws 31 and 32 reach to a set target value, the heating by the heating member 5 is continued and the coagulation and the resection by using the thermal surgical knife is performed. At step S5, if, the measured temperatures do not reach to the set target value, the control circuit 194 realizes and determines that. Then, at step S6, the control circuit 194 supplies a predetermined bipolar output to electrode portions 71 and 72 of the jaws 131 and 32 for a predetermined period of time by operating the bipolar electric surgical knife circuit 192. Thus, the control circuit 194 can cause the temperature of the living-body tissue grasped by the jaws 131 and 32 to reach to the target value for a short period of time.

After that, once the temperature reaches to the target value, at step S7, the control circuit 194 controls the power supply circuit 191 for the thermal surgical knife to supply power to the heating member 5 for the thermal surgical knife. Then, the coagulation and the resection are performed.

According to the invention, the generator 109 supplies an additional energy to the forceps body 101 based on measured temperature data. Thus, the operator does not have to manipulate the apparatus especially, but the living-body tissue can be coagulated and resected smoothly under various circumstances.

Figure 7:
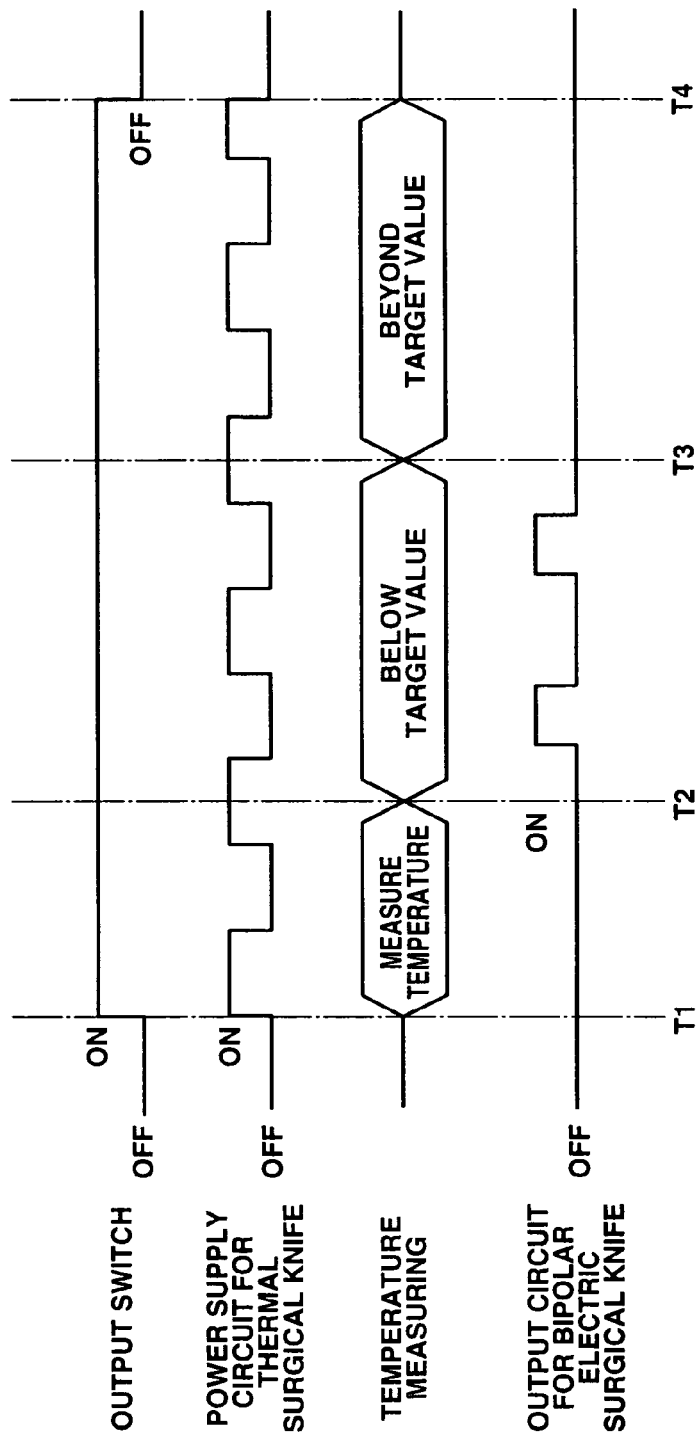
FIG. 7A is a diagram showing ON/OFF of an output switch in a timing chart for another control example of the control circuit of FIG. 5.
FIG. 7B is a diagram showing an output of power supply circuit for a thermal surgical knife in a timing chart of another control example of the control circuit of FIG. 5.
FIG. 7C is a diagram showing temperature measurement by a detecting circuit in a timing chart of another control example of the control circuit of FIG. 5.
FIG. 7D is a diagram showing an output of an output circuit for a bipolar electric surgical knife in a timing chart of another control example of a control circuit in FIG. 5.

FIGS. 7A to 7D are timing charts in another example of control by the control circuit 194 in FIG. 5. FIG. 7A shows ON/OFF of the output switch 200. FIG. 7B shows an output from the power supply circuit 191 for the thermal surgical knife. FIG. 7C shows temperature measurement by the detecting circuit 193. FIG. 7D shows an output from the output circuit 192 for the bipolar electric surgical knife.

In FIG. 7A, when the output switch 200 is OFF, the power supply circuit 191 for the thermal surgical knife, the detecting circuit 193 and the output circuit 192 for the bipolar electric surgical knife shown in FIGS. 7B, 7C and 7D are all turned OFF.

When the output switch 200 is turned ON at timing T1 as shown in FIG. 7A, the power supply circuit 191 for the thermal surgical knife shown in FIG. 7B is turned ON and OFF alternately. Then, the power supply circuit 101 for the thermal surgical knife supplies power to the heating member 5 for the thermal surgical knife and causes the heating member 5 for the thermal surgical knife to generate heat. Then, the detecting circuit 193 as shown in FIG. 7C measures the temperature.

From timing T1 to timing T2, the output circuit 192 for the bipolar electric surgical knife shown in FIG. 7D is turned OFF.

From timing T2, when the temperature measurement result by the detecting circuit 193 shown in FIG. 7C does not reach to the target value, that is, when the output of the bipolar electric surgical knife is required based on the temperature measurement result, the power supply circuit 191 for the thermal surgical knife shown in FIG. 7B and the output circuit 192 for the bipolar electric surgical knife shown in FIG. 7D output alternately in a time-division manner. From timing T3 to T4, when the temperature measurement result by the detecting circuit 193 excesses the target value, only the power supply circuit 191 for the thermal surgical knife shown in FIG. 7B is switched to output.

Therefore, in the control example shown in FIGS. 7A to 7D, when the output of the bipolar electric surgical knife is required, the total power consumption from the generator 109 in a unit period of time can be suppressed. Thus, the power supply circuit for the generator 109 can be minimized.

Third Embodiment

Figure 8:
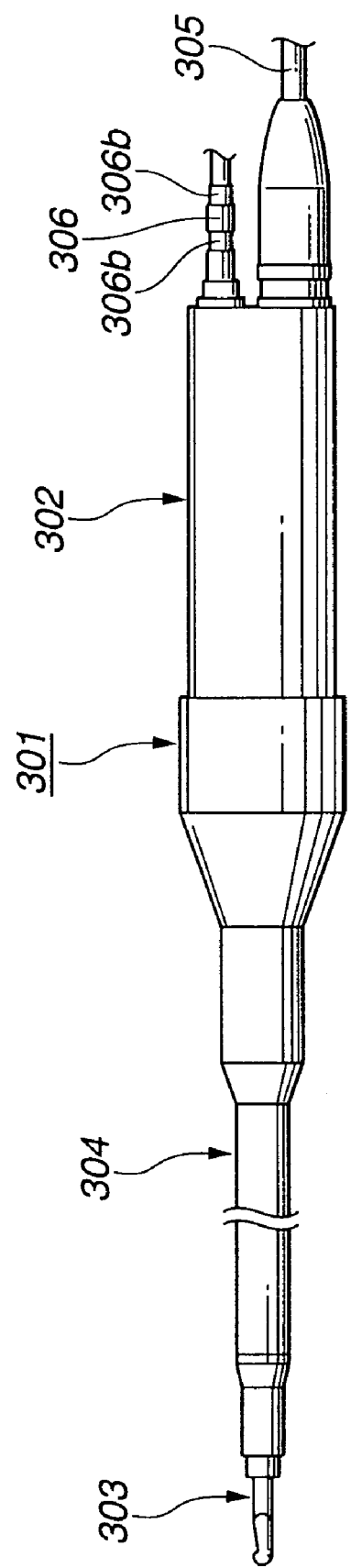
FIG. 8 is a side view of an ultrasound treating device according to a third embodiment of the present invention.
Figure 10A:
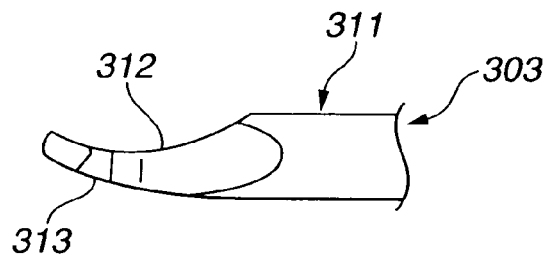
FIG. 10A is a plan view of a distal end treating portion of FIG. 9A.
Figure 10B:
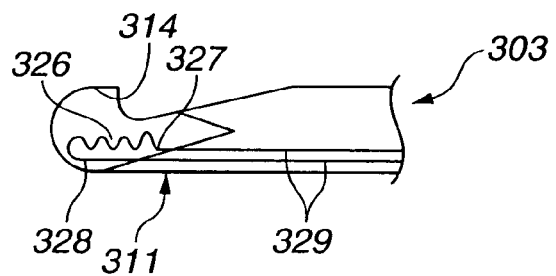
FIG. 10B is a side view of a distal end treating portion of FIG. 10A.

FIGS. 8 to 10B relate to a third embodiment of the present invention. FIG. 8 is a side view of an ultrasound treating device. FIG. 9A is an essential part sectional view of the ultrasound treating device of FIG. 8. FIG. 9B is a diagram showing a relationship between amplitude and a wavelength of FIG. 9A. FIG. 9C is a development of a flexible substrate of FIG. 9A. FIG. 9D is a sectional view of the flexible substrate of FIG. 9C. FIG. 10A is a plan view of a distal end treating portion of FIG. 9A. FIG. 10B is a side view of a distal end treating portion of FIG. 10A.

In FIGS. 8 to 10B, an ultrasound treating device 301 includes a vibrator 302, which ultrasound-vibrates as a treating energy generator upon energization, a probe 303 as a treatment device, which transmits ultrasound vibration generated by the vibrator 302, and a sheath 304, which covers the portion except a distal end treating portion of the probe 303.

In the ultrasound treating device 301, a cord 305 for supplying current to the vibrator 302 extends to the back end. The cord 305 is connected to a power supply body, not shown, which is a control device. In the ultrasound treating device 301, a connecting pin 306 for energizing a heat generating portion, described later, is projected at the back end. The connecting pin 306 is provided with connecting electrodes 306a and 306b, which are insulated from each other. Thus, a connecting cord to be connected to a heat generating power supply, not shown, can be attached thereto. The heat generating power supply may be provided in the power supply body.

That is, the ultrasound treating device 301 is connected to the power supply body and the heat generating power supply, which forms a treating apparatus.

A horn 307, which transmits ultrasound vibration generated by the vibrator 302 is fixed at the distal end of the vibrator 302. The horn 307 extends the amplitude by reducing the cross section. The horn 307 is provided with an internal screw portion 308 connecting the probe 303 to the distal end. The probe 303 is provided with an external screw portion 309, which can be screwed to the internal screw portion 308 removably. A notch portion 310 for associating a tool used to screw the horn 307 is formed in the probe 303.

As shown in FIG. 9B, the length of the probe 303 is set to n times of a half wavelength $\lambda/2$ of the vibration frequency (where $\lambda$ is a wavelength, and n is an integer). Thus, a distal end treating portion 311 is positioned just at the node of the vibration.

The probe 303 is provided, at the distal end, with the distal end treating portion 311 for resecting/coagulating living-body tissue. Rings 315a and 315b for positioning the probe 303 with respect to the internal surface of the sheath 304 is mounted at a position, which is the closest to the node, of the distal end treating portion 311. These rings 315a and 315b are formed by an electrically conductive and elastic member. The probe 303 is covered by the sheath 304 from the back end portion of the distal end treating portion 311 to the vibrator 302.

The sheath 304 includes an electrically-insulating inserting portion 316 to be inserted into a body cavity and an electrically-insulating holding portion 317 to be held by an operator. These inserting portion 316 and holding portion 317 are connected and fixed to each other. Distal end members 320 and 321 are connected to the inserting portion 316. The outside diameters of the distal end members 320 and 321 are narrowed down to the distal end of the inserting portion 316.

The inserting portion 316 is provided with a flexible substrate 323 inside. FIG. 9C is a diagram in which the flexible substrate 323 is developed. In practice, the flexible substrate 323 is arranged in a cylinder form. In FIG. 9D, the flexible substrate 323 is provided with conductors 323e and 323f, which are formed by copper foil, in layers of a reinforcing plate 323a and a cover plate 323d, each of which is formed from a resin sheet of polyimide, an adhesive 323b and an adhesive 323c.

A thorough-hole 323g is provided in the distal end side of the flexible substrate 323. The flexible substrate 323 is provided with electrode lands 324a and 324b formed by noble metal having good conductivity, such as nickel and gold. In addition, the flexible substrate 323 is provided with electrode lands 325a and 325b also in the proximal end.

The electrode lands 324a and 325a and 324b and 325b are connected by a wiring pattern 322 (not exposed in the surface), which is extended from the conductors 323e and 323f in the laminate. The electrode lands 324a and 324b contact and are electrically connected with the rings 315a and 315b within the sheath 304. The electrode lands 325a and 325b are also electrically connected to the connecting electrodes 306a and 306b through an energizing unit (not shown) such as a lead line within the holding portion 317.

As shown in FIGS. 10A and 10B, the distal end treating portion 311 has curved surfaces 312 and 313 on both sides, whose both surfaces are curved in larger radius of curvature toward the same direction. The distal end treating portion 311 is provided with a hook 314 by forming a notch in one side of the edge of the curved surfaces 312 and 313. The notch forming the hook portion 314 is formed by having a gentle gradient from the bottom surface of the concave portion of the hook portion 314 toward the root side of the distal end treating portion 311. The curved surface 313 is provided with a heat generating portion 326 as an electric resistor pattern by using a thin film forming technology such as sputtering and a thick film forming technology such as a printing method.

In the heat generating portion 326, the material of the electric resistor of the thin film is made from molybdenum or tungsten. A thin film formed from $Si_3N_4$ or the like is needed as an electrically insulating layer against the curved surface 313 and the external environment. The material of the electric resistor, which is a thick film, of the heat generating portion 326 is generally silver. Thus, $SiO_2$ is needed as an electrical insulating layer against the curved surface 313 and the external environment.

The heat generating portion 326 is electrically connected to the rings 315a and 315b through a wiring portion 329 (which is also covered by an insulating layer) whose end portions 327 and 328 are provided on the surface of the probe 303. The rings 315a and 315b are provided at the node of vibration. As a result, the amplitude is small, so that it is good for electrical connection.

Next, effects of the third embodiment will be described.

In order to resect living-body tissue, an operator ultrasound-vibrates the probe 303 of the ultrasound treating device 301. In order to coagulate living-body tissue, the operator applies voltage from the heat generating power supply to the portion between the connecting electrodes 306a and 306b of the ultrasound treating device 301. Then, the ultrasound treating device 301 is energized in the order of the electrode lands 325a/325b to the wiring pattern 322 to the electrode lands, 324a/324b to the rings 315a and 315b to the heat generating portion 326. As a result, in the ultrasound treating device 301, the heat generating portion 326 generates heat by the electric resistor, and the curved surface 313 of the distal end treating device 11 is heated.

Then, when stopping bleeding and/or coagulating in living-body tissue is required, the coagulation is performed by energizing the heat generating portion 326 of the ultrasound treating device 301 to heat the curved surface 313 of the distal end treating portion 311.

Therefore, the ultrasound treating device 301 according to this embodiment can selectively perform coagulation, resection and the like on living-body tissue by using ultrasound energy and heat generating energy. Effective treatment using the respective advantages is possible.

Unlike the electric surgical knife, the ultrasound treating device 301 according to this embodiment does not flow current to the living-body tissue during the coagulation. In addition, the ultrasound treating device 301 according to this embodiment can prevent living-body tissue from burning on because of the ultrasound vibration after coagulation. The ultrasound treating device 301 according to this embodiment can perform coagulation easily since the curved surface 313 of the distal end treating portion 311 has a form, which can be abutted on the living-body tissue easily.

Fourth Embodiment

Figure 11A:
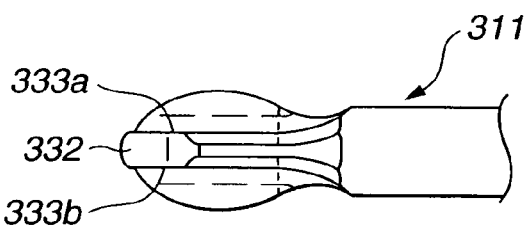
FIG. 11A is a plan view of a distal end treating portion of an ultrasound treating device according to a fourth embodiment of the present invention.
Figure 11C:
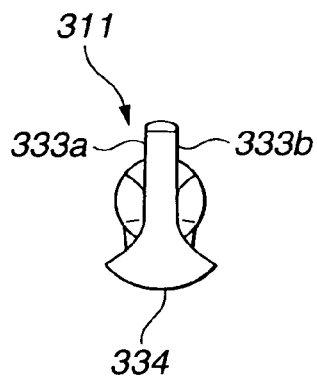
FIG. 11C is a front view of the distal end treating portion of FIG. 11A.
Figure 11B:
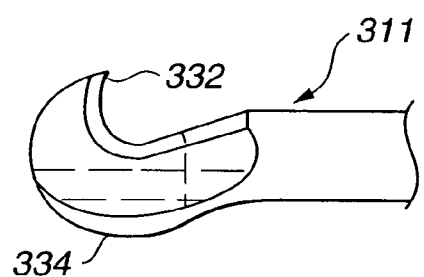
FIG. 11B is a side view of a distal end treating portion of FIG. 11A.
Figure 11D:
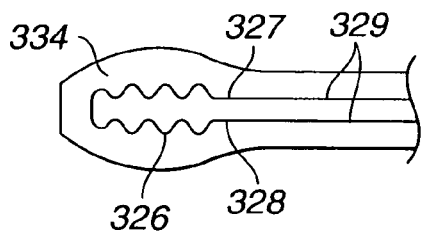
FIG. 11D is a bottom surface diagram of the distal end treating portion of FIG. 11A.

FIGS. 11A to 11D relate to a fourth embodiment of the present invention. FIG. 11A is a plan view of a distal end treating portion of an ultrasound treating device according to a fourth embodiment of the present invention. FIG. 11B is a side view of a distal end treating portion of FIG. 11A. FIG. 11C is a front view of the distal end treating portion of FIG. 11A. FIG. 11D is a bottom surface diagram of the distal end treating portion of FIG. 11A.

The fourth embodiment is substantially the same as the third embodiment except that the shape of the hook and the position of the heat generating portion 326 are changed.

As shown in FIGS. 11A to 11D, the distal end treating portion 311 is provided with plain portions 333a and 333b, which are parallel with the both sides of a hook portion 332.

In addition, the distal end treating portion 311 is provided with a curved surface portion 334. The curved surface portion 334 is provided with the heat generating portion 326.

The ultrasound treating device according to the fourth embodiment can use the hook portion 332 as a spatula, which is mainly effective for the resection of palisade tissue. The ultrasound treating device according to the fourth embodiment can resect living-body tissue by using the curved surface portion 334. The effect of the fourth embodiment is the same as the third embodiment.

Fifth Embodiment

Figure 12:
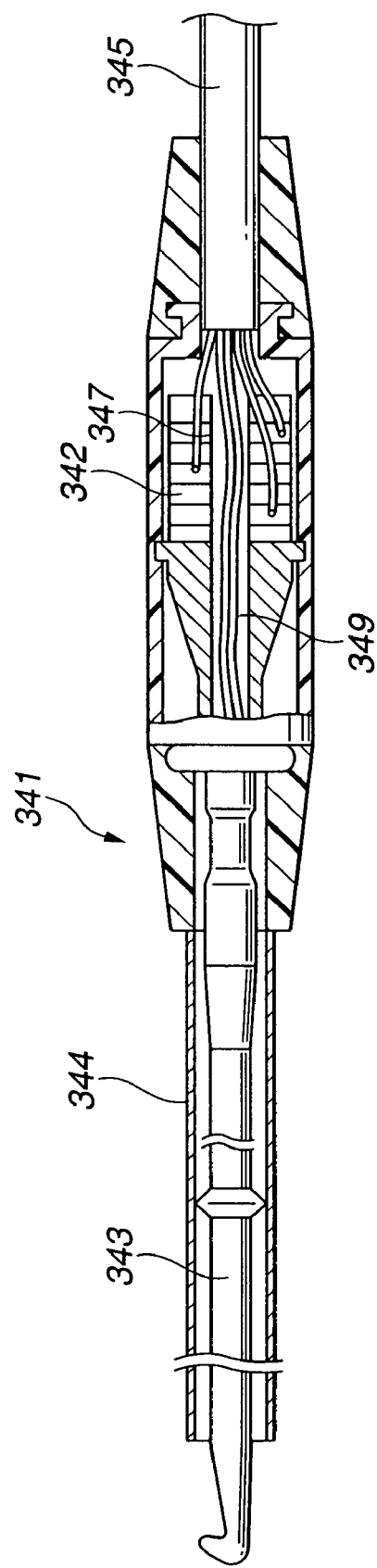
FIG. 12 is a longitudinal side view of an ultrasound treating device according to a fifth embodiment of the present invention.
Figure 13:
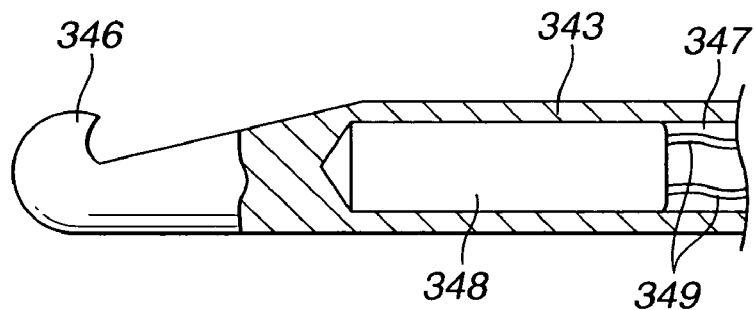
FIG. 13 is a sectional view of a distal end treating portion of FIG. 12.

FIGS. 12 and 13 relate to a fifth embodiment of the present invention. FIG. 12 is a longitudinal sectional view of an ultrasound treating device. FIG. 13 is a sectional view of a distal end treating portion of FIG. 12.

As shown in FIG. 12, an ultrasound treating device 341 according to the fifth embodiment includes a vibrator 342, which ultrasound-vibrates as a treating energy generator upon energization, a probe 343, which transmits ultrasound vibration generated by the vibrator 342, and a sheath 344, which covers the probe 343.

In the ultrasound treating device 341, a cord 345 for supplying current to the vibrator 342 extends to the back end. The cord 345 is connected to a power supply body, not shown, which is a control device. That is, the ultrasound treating device 341 together with the power supply body constitutes the treating apparatus.

In the ultrasound treating device 341, the vibrator 342 and the probe 343 are formed in the hollow structure.

As shown in FIG. 13, a hole 347 is formed to a position near the distal end processing portion 346 in the probe 343. The hole 347 is provided with a cylinder-shaped heater 348, which is a heat generating portion, at the back end portion.

Two lead lines 349, for energization, of the heater 348 extend from the cord 345 through the hole 347. Desirably, the heater 348 is a cartridge heater or a cylinder ceramic heater having a coil-shaped Nichrome wire inside.

The ultrasound treating device 341 according to the fifth embodiment ultrasound-vibrates the probe 343 in order to resect living-body tissue. The ultrasound treating device 341 according to the fifth embodiment energizes the heater 348 in order to coagulate the living-body-tissue. Then, the heat generated by the heater 348 is transmitted to the distal end treating portion 346. Thus, the distal end treating portion 346 is heated.

In this way, the ultrasound treating device 341 according to the fifth embodiment directly energizes the heater 348 through the lead line 349, which reduces the energization loss during the energization process. Thus, the efficiency is better than those of the third and fourth embodiments.

Sixth Embodiment

Figure 14:
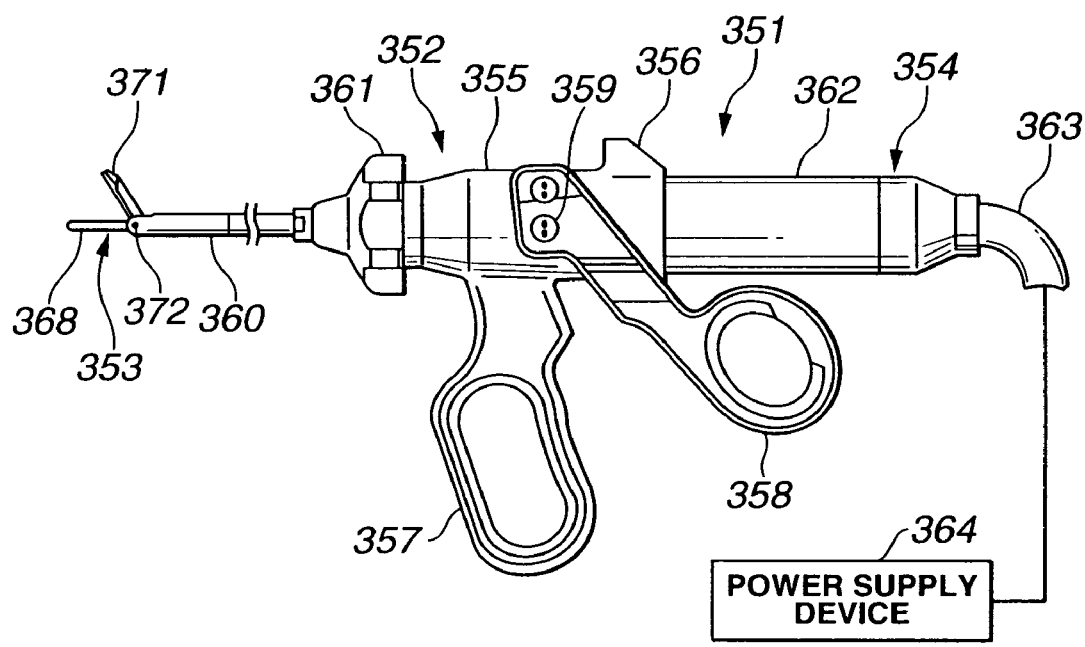
FIG. 14 is an entire configuration diagram showing an ultrasound coagulation/resection device according to a sixth embodiment of the present invention.
Figure 15:
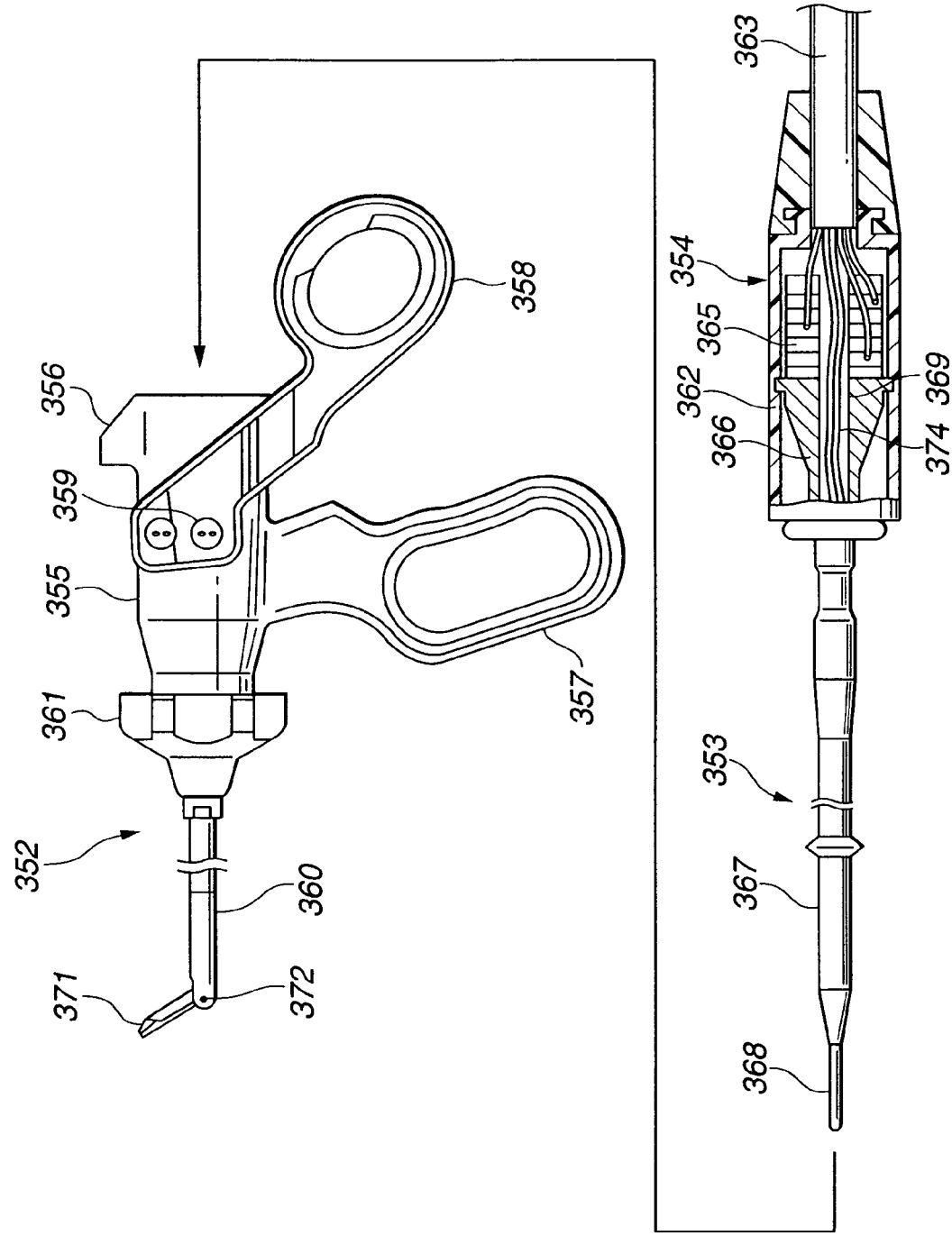
FIG. 15 is a side view of an operating portion body and a partial sectional view of a probe unit when a hand piece of FIG. 14 is exploded.
Figure 16:
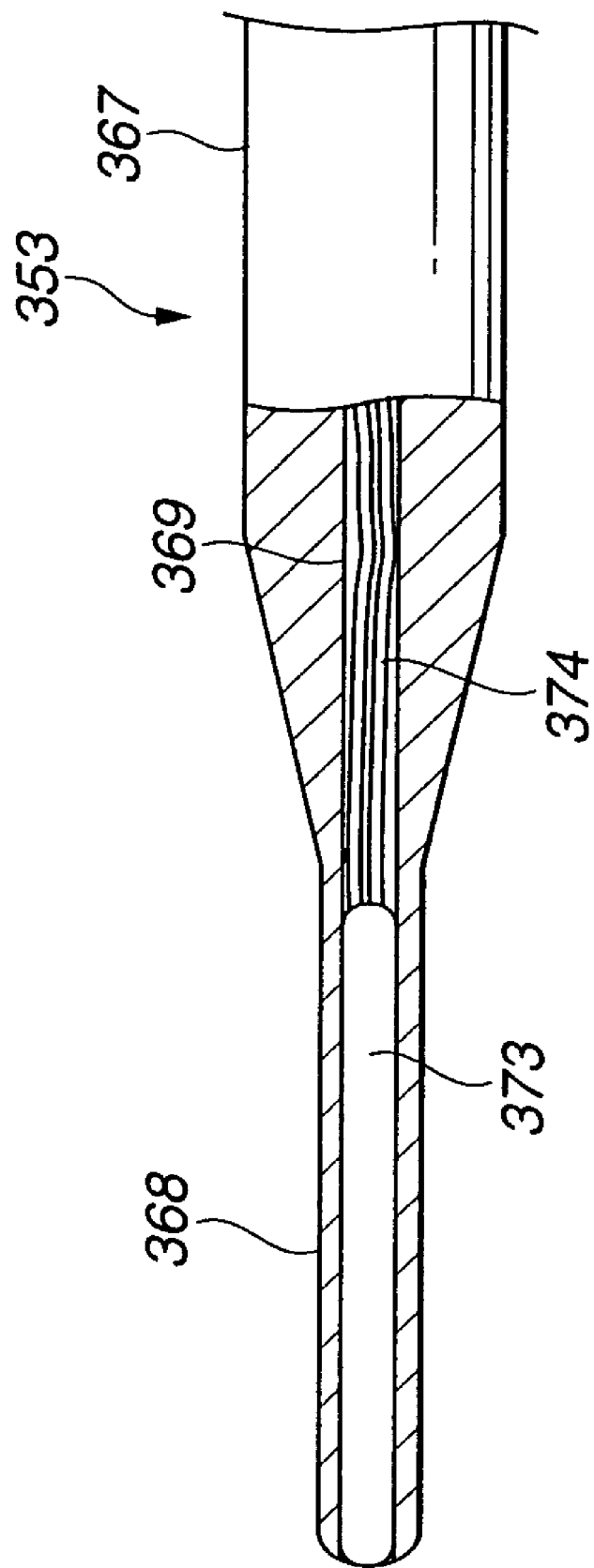
FIG. 16 is a sectional view of a distal end portion of a probe unit of FIG. 15.

FIGS. 14 to 16 relate to a sixth embodiment of the present invention. FIG. 14 is an entire configuration diagram showing an ultrasound coagulation/resection device. FIG. 15 is a side view of an operating portion body and a partial sectional view of a probe unit when a hand piece of FIG. 14 is exploded. FIG. 16 is a sectional view of a distal end portion of a probe unit of FIG. 15.

As shown in FIG. 14, an ultrasound coagulation/resection device according to the sixth embodiment includes a hand piece 351, which is a treating device. The hand piece 351 includes a handle unit 352, a probe unit 353 and a vibrator unit 354. The hand piece 351 is connected to a power supply device 364 as a control unit described later, which form the ultrasound coagulation/resection device.

The handle unit 352 is provided with an operating portion body 356 having a vibrator holding portion 355, a stationary handle 357, which is fixed at the front side of the operating portion body 356, and a rotatable and movable handle 358 at the rear side. Here, the movable handle 358 is rotatably supported to the operating portion body 356 by a shaft pin 359.

Furthermore, a proximal end portion of a long and narrow inserting sheath portion 360 is linked to the distal end of the operating portion body 356 through a rotatable knob 361. Here, the inserting sheath portion 360 and the rotatable knob 361 are mounted to the operating portion body 356 coaxially and rotatably.

As shown in FIG. 15, an ultrasound vibrator 365, which is an ultrasound vibration generating portion as a treating energy generator, is located under a cover 362 in the vibrator unit 354. The ultrasound vibrator 365 includes an element for converting electric signals to mechanical vibration. The ultrasound vibrator 365 is provided with a horn 366 at the front. The ultrasound vibrator 365 extends the amplitude by reducing the cross section of the horn 366. A cord 363 connected to the power supply device 364 is electrically connected to the ultrasound vibrator 365.

The probe unit 353 is provided with a stick-shaped probe 367, which is a vibration conducting member for conducting ultrasound vibration. The probe 367 may be made of a titan or aluminum material. The probe 367 is provided with, at the distal end, a treating portion 368 for contacting with living-body tissue. The treating portion 368 is formed by narrowing down the cross section so as to extend the amplitude.

Here, the hand piece 351 has the treating portion 368, which is projected from the distal end portion of the inserting sheath portion 360 to the outside. In this case, units are assembled together as shown in FIG. 14. Then, the hand piece 351 is provided with, at the distal end portion of the inserting sheath portion 360, a jaw 371, which is a grasp member supported so as to be able to grasp living-body tissue by sandwiching with the treating portion 368. The jaw 371 is axially supported at the distal end portion of the inserting sheath portion 360 by using a fulcrum pin 372 at the base end portion.

Furthermore, a wire-shaped drive shaft, not shown, which is used to operate the jaw 371, is located inside of the inserting sheath portion 370. A base end portion of the jaw 371 is linked to the distal end portion of the drive shaft of the inserting sheath portion 370. The base end portion of the drive shaft is linked to the movable handle 358. Then, the drive shaft is manipulated to back and forth by sandwiching with a manipulation of the movable handle 358. Thus, the jaw 371 is pivoted with respect to the fulcrum pin 372. Then, the jaw 371 is opened or closed with respect to the treating portion 368. Thus, the jaw 371 is supported so as to grasp living-body tissue by sandwiching with the treating portion 368.

As shown in FIG. 15, the ultrasound vibrator 365, the horn 366 and the probe 367 have a hollow structure, and a hole 369 passes therethrough. A cylinder heater 373, which is a heat generating portion, is provided inside of the treating portion 368. In the heater 373, two lead lines 374 extend from the cord 363 through the hole 369. The heater 373 is preferably a cylinder-shaped ceramic heater or a cartridge heater having a coil-shaped Nichrome wire in the internal tube.

Next, effects of the sixth embodiment will be described.

An operator grasps living-body tissue by using the jaw 371 for ultrasound coagulation/resection. The operator ultrasound-vibrates the probe 367 and the treating portion 368 and coagulate and resect the living-body tissue by using the generated friction heat. In order to perform coagulation only to stop bleeding from living-body tissue, the heater 373 is energized. Then, the heat generated by the heater 373 is conducted to the treating portion 368. Then, the operator causes the treating portion 368 to contact with the living-body tissue such that the coagulation can be performed by using the heat generation by the treating portion 368. Furthermore, the operator can cause the heater 373 to generate heat for ultrasound coagulation/resection.

According to this embodiment, the ultrasound coagulation/resection apparatus can perform coagulation only certainly by causing the heater 373 to generate heat. The treating speed of the ultrasound coagulation/resection apparatus according to this embodiment can be improved significantly by using both of the ultrasound treatment and the heating treatment by using the heater 373. Furthermore, the construction of the ultrasound coagulation/resection apparatus according to this embodiment can be simplified by partially sharing the means for energizing the heater 373 with the means for energizing the vibrator.

Seventh Embodiment

Figure 17:
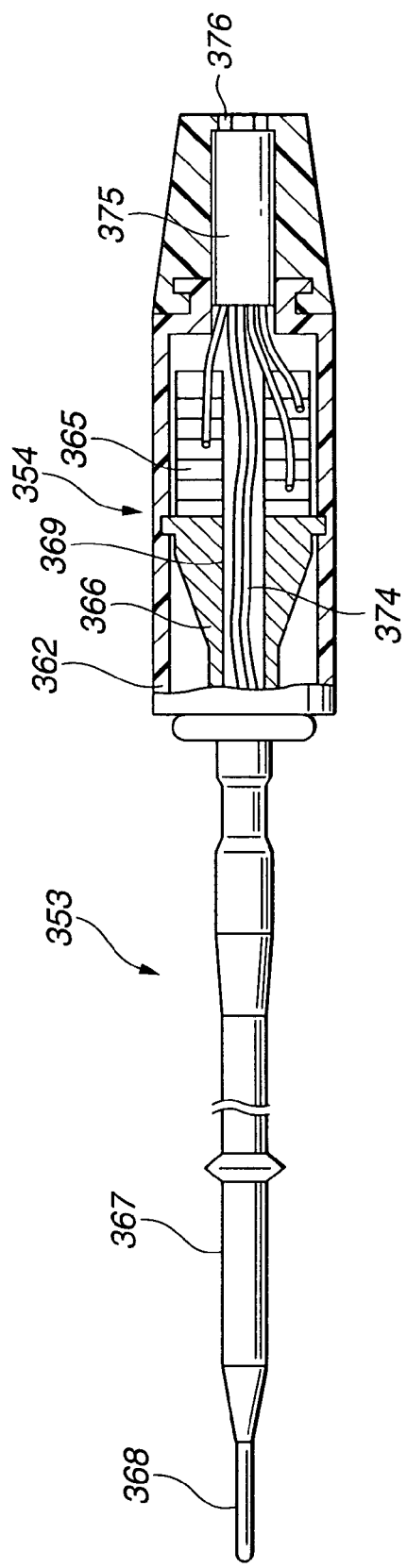
FIG. 17 is a longitudinal sectional view of a probe unit and a vibrator unit of an ultrasound coagulation/resection apparatus according to a seventh embodiment of the present invention.

FIG. 17 relates to a seventh embodiment of the present invention. FIG. 17 is a longitudinal sectional view of a probe unit and a vibration unit of an ultrasound coagulation/resection apparatus. Identical reference numerals are given to identical components of the sixth embodiment, and the description will be omitted here.

A vibrator unit 354 is provided with a chargeable battery unit 375. The battery unit 375 may be a nicad battery or a lithium ion battery. The battery unit 375 is further provided with a terminal 376 for charging. The battery unit 375 is turned ON/OFF by using a switch unit, not shown. Since the battery unit 375 is hard to set the output, only the energization to the heater 373 may be performed.

According to this embodiment, a need for a cord is eliminated since the battery unit is provided therein. Thus, the operability is improved.

Eighth Embodiment

Figure 18:
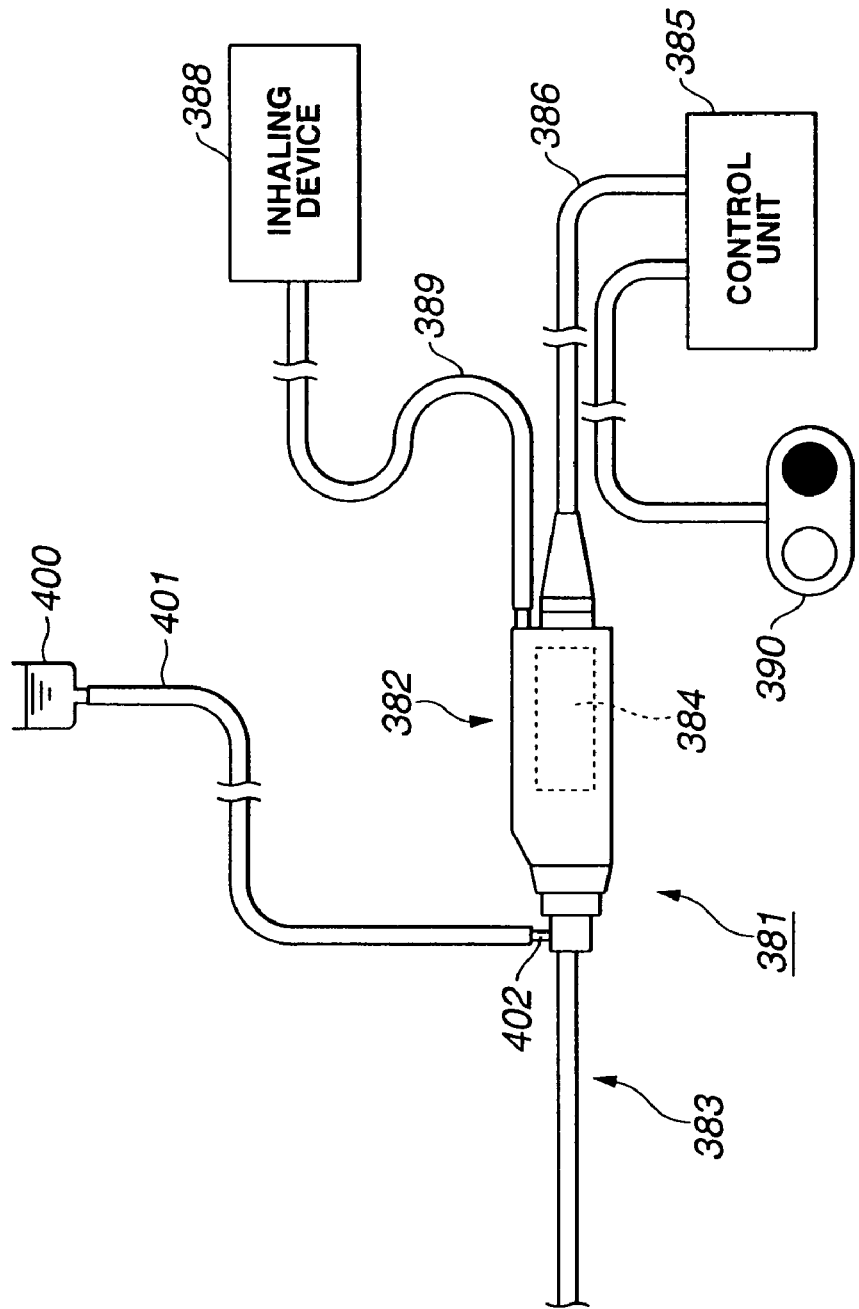
FIG. 18 is an entire configuration diagram of a surgical resecting apparatus according to an eighth embodiment of the present invention.
Figure 19A:
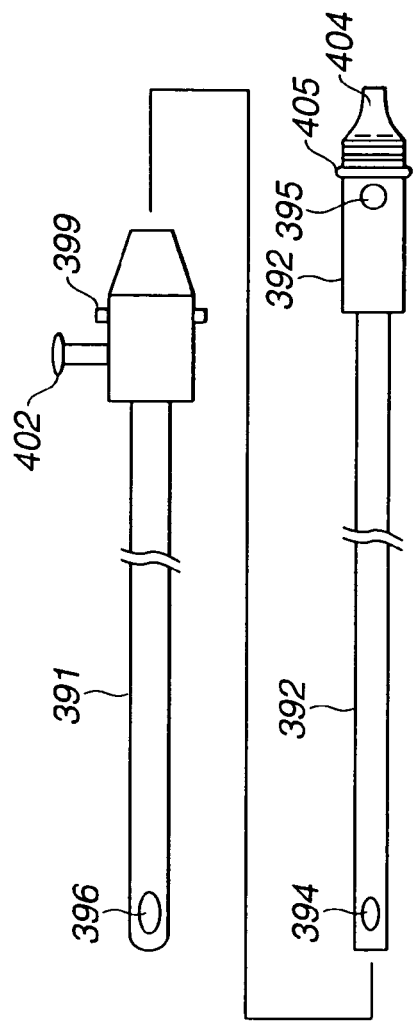
FIG. 19A is a diagram in which internal tubes and external tubes of the surgical resecting device of FIG. 18 are exploded.
Figure 19B:
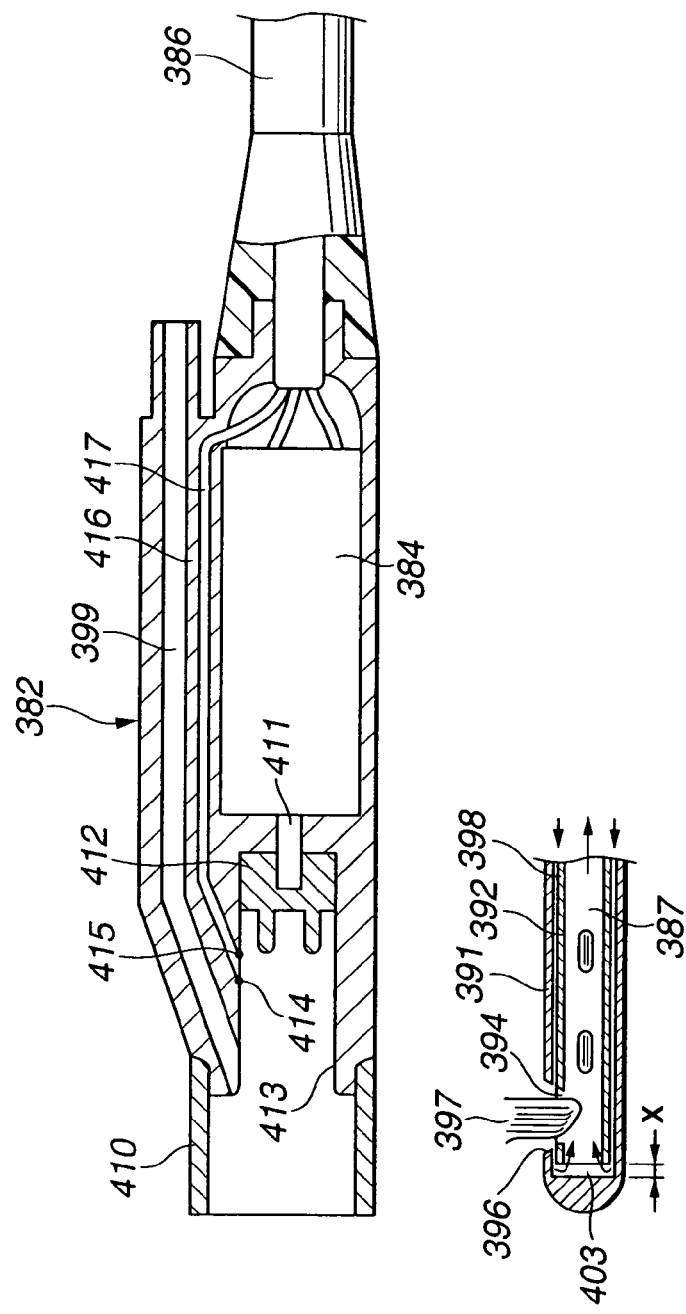
FIG. 19B is a sectional view of a hand piece body of FIG. 18.
Figure 19C:
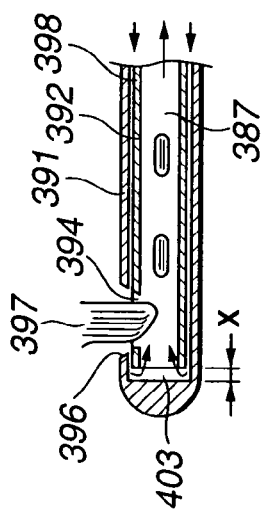
FIG. 19C is a distal end sectional view of the surgical resecting device of FIG. 18.
Figure 20:
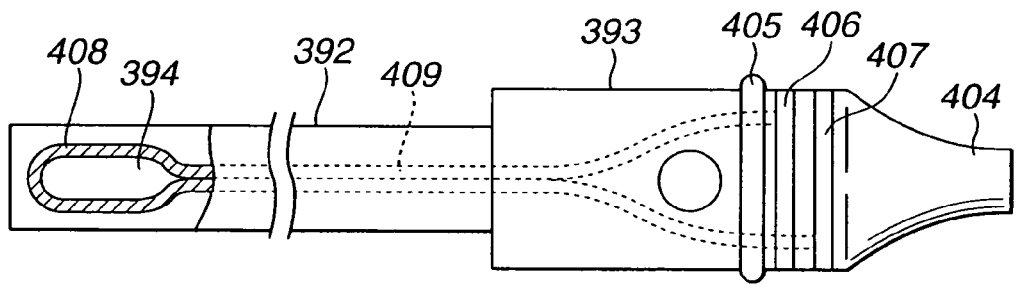
FIG. 20 is a side view of the internal tube of FIG. 19A.

FIGS. 18 to 20 relate to an eighth embodiment of the present invention. FIG. 18 is an entire configuration diagram of a surgical resecting apparatus. FIG. 19A is a diagram in which internal tubes and external tubes of the surgical resecting device of FIG. 18 are exploded. FIG. 19B is a sectional view of a hand piece body of FIG. 18. FIG. 19C is a distal end sectional view of the surgical resecting device of FIG. 18. FIG. 20 is a side view of the internal tube of FIG. 19A.

As shown in FIG. 18, a surgical resecting apparatus (called "resecting apparatus" hereinafter) 381 includes a hand piece 382 and an inserting portion 383. The hand piece 382 has a motor 384 built-in. The motor 384 is connected to a control unit 385, which is a control device, through a cable 386. An inhaling path provided in the inserting portion 383 is connected to an inhaling device 388, which generates inhaling pressure, through an inhaling tube 389.

In other words, the resecting apparatus 381 is connected to the control unit 385 and the inhaling apparatus 388 in order to form a surgical resecting apparatus. A foot switch 390 is connected to the control unit 385.

As shown in FIGS. 19A to 19C and FIG. 20, the inserting portion 383 has a dual tube structure including an external tube 391 and an internal tube 392. The internal tube 392 is formed from metal such as stainless. The internal tube 392 is provided with, in the proximal end, a connecting portion 393, which can be connected to the hand piece 382 freely removably. The connecting portion 393 is provided with a tongue edge 404 and can rotate by engaging with the motor 384 within the hand piece 382. An intake 395 is formed in the connecting portion 393. The intake 395 is communicated to an opening 394 formed on the side surface of the distal end portion of the internal tube 392 and the inhaling path 387 formed all over the length of the internal tube 392. The intake 395 is linked to the inhaling path 399 provided within the hand piece 382 and the external inhaling device 388.

The connecting portion 393 is provided with an O-ring 405 for water tightness in the proximal end of the intake 395. The connecting portion 393 is provided with electrodes 406 and 407 all around the O-ring 405 in the proximal end. Here, around the connecting portion 393 and the opening 394, a heat generating portion 408 is provided as an electric resister pattern by using a thin film forming technology such as sputtering or a thick film forming technology such as a printing method.

The heat generating portion 408 is generally made of molybdenum or tungsten and needs a thin film formed of $Si_3N_4$, for example, as an electric insulating layer against the internal tube 392 and the external environment. FIG. 20 indicates a state where the electrical insulating layer around the opening is removed. Generally, the heat generating portion 394 is hard to see from the outside because of the electrical insulating layer. The material of the thick electrical resistor is generally silver. The electrical insulating layer against the internal tube 392 and the external environment is generally made of $SiO_2$. The heat generating portion 408 is electrically connected to the electrodes 406 and 407 through a wire 409 extending to the proximal end.

As shown in FIGS. 19A to 19C, the distal end of the external tube 391 is formed in sphere in order to improve the stability. An opening 396 is formed inside the external tube 391 at the same position in the longitudinal direction as that of the opening 394 of the internal tube 392. Blades are formed at the edges of the opening 396 of the external tube 391 and the opening 394 of the internal tube 392, respectively. Through the rotational movement of the internal tube 392, these blades are adjusted to collaborate and cut living-body tissue 397, which is inhaled and captured into the openings 394 and 396, into small pieces of tissue. In other words, the motor 384 functions as a treatment energy generator, which makes the internal tube 392 to rotate as treatment energy for resecting living-body tissue.

In the resecting apparatus 381, a ring-shaped gap is formed for flowing perfusion fluid over the substantially all length between the external tube 391 (inner surface) and the internal tube 392 (outer surface). The gap constitutes a water feeding duct 398. The resecting apparatus is provided with a link member 399 in the proximal end of the external tube 391. The internal tube 392 is linked so as to be able to rotate watertightly with respect to the external tube 391. The link member 399 is provided with water outlet 402. The water outlet 402 is connected to an external water feeding bottle 400 (see FIG. 18) through a water feeding tube 401. Thus, the perfusion fluid accommodated within the water feeding bottle 400 is supplied to the distal end of the inserting portion 383 through the water feeding tube 401, water outlet 402 and water feeding duct 398.

The internal distal end of the external tube 391 and the distal end of the internal tube 392 are spaced by X in the axial direction as shown in FIG. 19C. Thus, the resecting apparatus 381 can prevent the contact between the external tube 391 and the internal tube 392 and smoothes the rotation of the internal tube 392. A flowing path 403 is formed such that the perfusion fluid flowing the water feeding duct 398 flows into the inhaling path 387 all the time.

The hand piece 382 is provided with a connecting portion 410 engaging with the link member 399 of the external tube 391 freely removably as shown in FIG. 19B. The motor 384 is provided with an output axis 411 projecting toward a lumen 413. The output axis 411 is provided, at the distal end side, with a connecting axis 412 engaging with a tongue edge 404 removably. Brushes 414 and 415 project toward the lumen 413. The brushes 414 and 415 are energized from wires 416 and 417, that are branched off from the cable 386.

When the internal tube 392 is engaged with the hand piece 382 as well as the external tube 391, the electrodes 406 and 407 contact and are electrically connected with the brushes 414 and 415. The internal wall of the lumen 413 has a structure preventing fluid from being invaded in the proximal end of the engaged O-ring 405.

Next, effects of the eighth embodiment will be described.

When the external tube 391 and the internal tube 392 are linked to the hand piece 382 during the use, the resecting apparatus 381 is also linked to the motor 384 and the internal tube 392. Then, an operator drives the motor 384 by using the foot switch 390. Then, the rotation of the motor 384 is conducted to the internal tube 392. In the resecting apparatus 381, living-body tissue to be resected is inhaled and is captured from the openings 394 and 396 by the inhaling caused by the operation of the inhaling device 388. The living-body tissue captured to the openings 394 and 396 are cut by the blades provided to the openings 394 and 396 by using the rotation of the internal tube 392. The cut tissue pieces are inhaled and are removed by the external inhaling device 388 through the inhaling path 387, the intake 395 and the inhaling tube 389.

Upon the resection of the living-body tissue, the perfusion fluid within the water feeding bottle 400 flows into the water feeding duct 398 through the water feeding tube 401 and the water feeding outlet 402 and is inhaled to the intake 387 through the flowing path 403. Therefore, in the resecting apparatus 381, the resected tissue pieces are certainly inhaled through the flow of the perfusion fluid inhaled into the inhaling path 387.

Here, in order to prevent bleeding when tissue is resected, the operator energizes the heat generating portion 408 from the control unit 385 through the wire 416, the brushes 414 and 415, and the electrodes 406 and 407 by manipulating the foot switch 390. The heat generating portion 408 causes resistance heat generation due to the energization to stop bleeding and to coagulate living-body tissue by heating living-body tissue upon resection.

According to this embodiment, the resecting apparatus 381 can prevent bleeding during resection without performing prevention such as high frequency noise shut-out.

Figure 21:
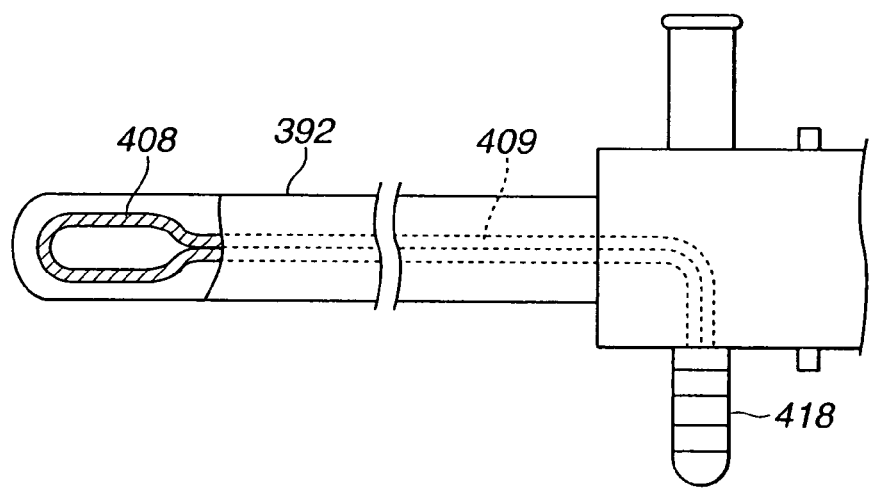
FIG. 21 is a diagram showing a first variation example of the eighth embodiment.

FIG. 21 shows a first variation example of the eighth embodiment.

The resecting apparatus in the first variation example has the heat generating portion 408 around the opening 396 in the external tube 391. The heat generating portion 408 is connected to a plug 418 through the wire 409. The plug 418 is energized through an energizing cable, not shown. According to the first variation example of this embodiment, the construction is further simplified than the eighth embodiment.

Figure 22:
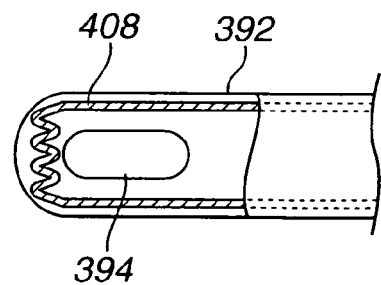
FIG. 22 is a diagram showing a second variation example of the eighth embodiment.

FIG. 22 shows a second variation example of the eighth embodiment.

A resecting apparatus in the second variation example, the heat generating portion 408 is provided in the distal end side of the opening 396 of the external tube 391.

The resecting apparatus in the second variation can stop bleeding by using the sphere-shaped distal end portion according to the above-described configuration. In addition, the heating treatment can be performed on a narrow area, and living-body tissue such as cartilage can be resected. It is easy and effective to use the resecting apparatus for not only the resection of a joint but also allergy treatment within a nose.

It is apparent to arrange different embodiments in wide ranges according to the present invention without departing from the spirit and the scope of the invention. The present invention is not limited by the specific embodiments. The present invention is only limited by the appended claims.

What is claimed is:

1. A treating apparatus comprising:
   a grasping portion configured to grasp a living-body tissue;
   a pair of electrodes provided in the grasping portion configured to apply high frequency current to the living-body tissue to heat the living-body tissue;
   a heat generating portion provided in the grasping portion configured to heat the grasping portion;
   a first switch configured to activate the heat generating portion;
   a second switch configured to activate the pair of electrodes;
   a temperature sensor configured to detect a temperature of the living-body tissue; and
   a control device configured
      to operate the first switch to activate the heat generating portion to perform heating for a predetermined time period, and
      if a temperature detected by the temperature sensor after heating by the heat generation portion for the predetermined time period has not reached a set temperature, to operate the first switch and the second switch to alternately perform heating by the heat generating portion and heating by the pair of electrodes in a time-division manner.

2. The treating apparatus according to claim 1, wherein the grasping portion is comprised of a pair of jaws openably supported so as to grasp the living-body tissue; and
   wherein the heat generating portion and the pair of electrodes are arranged in at least one of the pair of jaws.

3. The treating apparatus according to claim 1, wherein the heat generating portion is a resistor provided on a surface of the grasping portion.

4. The treating apparatus according to claim 3, wherein the resistor is a thin film resistor or a thick film resistor.

5. The treating apparatus according to claim 1, wherein the heat generating portion is one of a cartridge heater and a ceramic heater.

6. The treating apparatus according to claim 1, wherein the pair of electrodes are provided in grasping surfaces of the grasping portion, and the heat generating portion is provided in the inner part of the grasping portion.

7. The treating apparatus according to claim 1, wherein the first switch and the second switch can be selectively operated.

8. A treating device comprising:
a pair of jaws configured to grasp a living-body tissue, each of the jaws having a contact surface for contacting the living-body tissue;
a pair of electrodes exposed on the contact surfaces of the pair of jaws, respectively, configured to conduct high frequency current via the living-body tissue to heat the living-body tissue;
an electric-heater element configured to heat at least one of the pair of electrodes;
a control device configured to supply the high frequency current to the pair of electrodes and electric power convertible into heat by the electric-heater element to the electric-heater element;
a switch unit comprising:
  a first switch configured to control supply of high-frequency current to the pair of electrodes, and
  a second switch configured to control supply of electric power to the electric-heater element; and
a temperature sensor configured to detect a temperature of the living-body tissue,
wherein the control device is configured
  to operate the second switch to supply electric power to the electric-heater element for a predetermined time period to perform heating of the living-body tissue, and
  if a temperature detected by the temperature sensor after heating by the electric-heater element for the predetermined time period has not reached a set temperature, to operate the second switch to supply electric power to the electric-heater element and to operate the first switch to supply high frequency current to the pair of electrodes to alternately perform heating by the electric-heater element and heating by the pair of electrodes in a time-division manner.

9. The treating apparatus according to claim 8, wherein the first switch and the second switch can be selectively operated.

10. A treating device comprising:
a heat generating portion configured to generate heat to be applied to a living-body tissue;
an ultrasound vibrator configured to generate ultrasound vibration to be applied to the living-body tissue;
a treating portion configured to contact the living-body tissue and to apply to the living-body tissue the heat generated by the heat generated portion and the ultrasound vibration generated by the ultrasound vibrator;
a probe having the treating portion arranged therein, the probe being configured to conduct the heat generated by the heat generating portion and the ultrasound vibration generated by the ultrasound vibrator;
a temperature sensor configured to detect a temperature of the living-body tissue; and
a control device configured
  to control the heat generating portion to generate heat that is applied to the living-body tissue for a predetermined time period, and
  if a temperature detected by the temperature sensor has not reached a set temperature after heating by the heat generating portion for the predetermined time period, to control the heat generating portion to generate heat and to control the ultrasound vibrator to generate ultrasound vibration to alternately perform heating by the heat generating portion and heating by the ultrasound vibrator in a time division manner.

11. The treating device according to claim 10, wherein the treating portion has a grasp member supported openably so as to grasp the living-body tissues by sandwiching with a distal end portion of the probe and has the heat generating portion at a distal end of the probe.

12. The treating apparatus according to claim 11, wherein the probe is inserted through a sheath and is projected from a distal end of the sheath; and
wherein the grasp member is attached rotatably at the distal end of the sheath and grasps the living-body tissue by sandwiching with the distal end portion of the probe, which is projected from the distal end of the sheath.

13. The treating apparatus according to claim 10, further comprising:
a first switch for activating the heat generating portion; and
a second switch for activating the ultrasound vibrator;
wherein the first switch and the second switch can be selectively operated.

* * * * *